US006794174B2

(12) United States Patent
Pletnev et al.

(10) Patent No.: US 6,794,174 B2
(45) Date of Patent: Sep. 21, 2004

(54) FULL-LENGTH INFECTIOUS CDNA CLONES OF TICK BORNE FLAVIVIRUS

(75) Inventors: Alexander Pletnev, Rockville, MD (US); Robert M. Chanock, Bethesda, MD (US)

(73) Assignee: The United States of America as represented by the Department of Health & Human Services, Washington, DC (US)

( * ) Notice: Subject to any disclaimer, the term of this patent is extended or adjusted under 35 U.S.C. 154(b) by 0 days.

(21) Appl. No.: 10/207,745

(22) Filed: Jul. 26, 2002

(65) Prior Publication Data

US 2004/0033594 A1 Feb. 19, 2004

Related U.S. Application Data

(63) Continuation of application No. PCT/US01/04460, filed on Feb. 9, 2001.

(60) Provisional application No. 60/181,490, filed on Feb. 10, 2000.

(51) Int. Cl.[7] .......................... C12N 7/01; C12N 5/00; C12N 15/00; C07H 21/04; A61K 39/12

(52) U.S. Cl. ................ 435/235.1; 435/325; 435/320.1; 536/23.1; 424/204.1

(58) Field of Search ............................ 435/235.1, 325, 435/320.1, 5, 6, 69.1; 536/23.1, 237.2; 424/204.1

(56) References Cited

U.S. PATENT DOCUMENTS 6,010,894 A 1/2000 Barrett et al.

FOREIGN PATENT DOCUMENTS

RU 2070929 12/1996
WO WO 99/18216 4/1999

OTHER PUBLICATIONS

Campbell, M. S., et al. (2000) Infectious cDNA Clones of Langat Tick–Borne Flavivirus That Differ from Their Parent in Peripheral Neurovirulence. Virology 269:225–237.

Iacono–Connors, L. C. & Schmaljohn, C. S. (1992) Cloning and Sequence Analysis of the Genes Encoding the Non-structural Proteins of Langat Virus and Comparative Analysis with other Flaviviruses. Virology 188:875–880.

Levkovich, E. N., et al., (1981) Characteristics of Immunogenesis in Monkeys Infected with Attenuated Tick–Borne Encephalitis and Langat Virus Strains, Voprosy Virusologii 2:160–164 XP001018713 (Abstract).

Mandl, C. W., et al. (1991) Sequence of the Genes Encoding the Structural Proteins of the Low–Virulence Tick–Borne Flaviviruses Langat TP21 and Yelanstev. Virology 185:891–895.

Mandl, C. W., et al. (1998) Spontaneous and Engineered Deletions in the 3' Noncoding Region of Tick–Borne Encephalitis Virus: Construction of Highly Attenuated Mutants of a Flavivirus. J. Virol. 72(3):2132–2140.

Pletnev, A. G., et al. (1992) Construction and characterization of chimeric tick–borne encephalitis/dengue type 4 viruses. PNAS USA 89:10532–10536.

(List continued on next page.)

*Primary Examiner*—Hankyel T. Park
(74) *Attorney, Agent, or Firm*—Knobbe, Martens, Olson & Bear LLP

(57) ABSTRACT

Embodiments described herein include full-length infectious cDNA clones of Langat tick-borne flavivirus.

20 Claims, 6 Drawing Sheets

OTHER PUBLICATIONS

Pletnev, A. G. & Men, R. (1998) Attenuation of the Langat tick–borne flavivirus by chimerization with mosquito–borne flavivirus dengue type 4. PNAS USA 95:1746–1751.

Pletnev, A. G., et al. (2000) Chimeric Langat/Dengue Viruses Protect Mice from Heterologous Challenge with the Highly Virulent Strains of Tick–Borne Encephalitis Virus. Virology 274:26–31.

Pletnev, A. G. (2001) Infectious cDNA Clone of Attenuated Langat Tick–Borne Flavivirus (Strain E5) and a 3' Deletion Mutant Constructed from It Exhibit Decreased Neuroinvasiveness in Immunodeficient Mice. Virology 282:288–300.

Sokolova, E. D., et al. (1994) Characterization of neruovirulence, stability, and immunogenicity of attenuated variants of TP–21 virus. Voprosy Virusologii 39(5):220–223 XP001018703 (Abstract).

| Size of deletion (nts) | Sequence of junction | Intermediate plasmid construct | Full-length E5 cDNA CLONE |
|---|---|---|---|
| 320 | 10,379 10,700<br>5'-CAATATTTTAAAGCCTTAAGAAACTTTGTG-3'<br>(SEQ. ID. NO.12) | p624-3'-320 | pE5-3'-320 |
| 374 | 10,379 10,754<br>5'-CAATATTTTAAAGCCTTAAGGCCCCCAGGG-3'<br>(SEQ. ID. NO.13) | p624-3'-374 | pE5-3'-374 |
| 449 | 10,379 10,829<br>5'-CAATATTTTAAAGCCTTAAGAAACTTTGTG-3'<br>(SEQ. ID. NO.14) | p624-3'-449 | pE5-3'-449 |
| 471 | 10,379 10,851<br>5'-CAATATTTTAAAGCCTTAAGGGGGGGCGGT-3'<br>(SEQ. ID. NO.15) | p624-3'-471 | pE5-3'-471 |

(FIG. II)

SEQUENCE LISTING

```
<160> NUMBER OF SEQ ID NOS: 15

<210> SEQ ID NO 1
<211> LENGTH: 75
<212> TYPE: DNA
<213> ORGANISM: Artificial Sequence
<220> FEATURE:
<223> OTHER INFORMATION: primer

<400> SEQUENCE: 1

gaaggtggtc tttgcggccg catcatacac atacgattta ggtgacacta tagagatttt     60

cttgcgcgtg catgc                                                      75


<210> SEQ ID NO 2
<211> LENGTH: 29
<212> TYPE: DNA
<213> ORGANISM: Artificial Sequence
<220> FEATURE:
<223> OTHER INFORMATION: primer

<400> SEQUENCE: 2

gggtgcatct cgacgcgtag gccggtacc                                       29


<210> SEQ ID NO 3
<211> LENGTH: 45
<212> TYPE: DNA
<213> ORGANISM: Artificial Sequence
<220> FEATURE:
<223> OTHER INFORMATION: primer

<400> SEQUENCE: 3

gcctgcggag ggtaccgata tcagcgggtg tttttccgag acacg                     45


<210> SEQ ID NO 4
<211> LENGTH: 22
<212> TYPE: DNA
<213> ORGANISM: Artificial Sequence
<220> FEATURE:
<223> OTHER INFORMATION: primer
```

-continued

<400> SEQUENCE: 4
ctatggccag gtggaaagcc gc 22

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
cccagggttg caagccccag 20

<210> SEQ ID NO 6
<211> LENGTH: 21
<212> TYPE: DNA
<213> ORGANISM: Artificial Sequence
<220> FEATURE:
<223> OTHER INFORMATION: primer

<400> SEQUENCE: 6
ttgcacctga ctgaactgga g 21

<210> SEQ ID NO 7
<211> LENGTH: 39
<212> TYPE: DNA
<213> ORGANISM: Artificial Sequence
<220> FEATURE:
<223> OTHER INFORMATION: primer

<400> SEQUENCE: 7
ttggactcct tgcttaaggc tttaaaatat tgagctctc 39

<210> SEQ ID NO 8
<211> LENGTH: 39
<212> TYPE: DNA
<213> ORGANISM: Artificial Sequence
<220> FEATURE:
<223> OTHER INFORMATION: primer

<400> SEQUENCE: 8
actgggcgtt atcttaaggc cccagggggg aaacccctg 39

<210> SEQ ID NO 9
<211> LENGTH: 39
<212> TYPE: DNA
<213> ORGANISM: Artificial Sequence
<220> FEATURE:
<223> OTHER INFORMATION: primer

<400> SEQUENCE: 9
ggatatttcc tccttaagat accaaatgtc ccctcgtca 39

<210> SEQ ID NO 10
<211> LENGTH: 39
<212> TYPE: DNA
<213> ORGANISM: Artificial Sequence
<220> FEATURE:
<223> OTHER INFORMATION: primer

<400> SEQUENCE: 10
cccctcgtca gacttaaggg ggggcggttc ttgttctcc 39

<210> SEQ ID NO 11
<211> LENGTH: 39

-continued

```
<212> TYPE: DNA
<213> ORGANISM: Artificial Sequence
<220> FEATURE:
<223> OTHER INFORMATION: primer

<400> SEQUENCE: 11

acggacgtgc gccttaagaa actttgtgag accccttgc                          39


<210> SEQ ID NO 12
<211> LENGTH: 30
<212> TYPE: DNA
<213> ORGANISM: Artificial Sequence
<220> FEATURE:
<223> OTHER INFORMATION: primer

<400> SEQUENCE: 12

caatatttta aagccttaag aaactttgtg                                    30


<210> SEQ ID NO 13
<211> LENGTH: 30
<212> TYPE: DNA
<213> ORGANISM: Artificial Sequence
<220> FEATURE:
<223> OTHER INFORMATION: primer

<400> SEQUENCE: 13

caatatttta aagccttaag gcccccaggg                                    30


<210> SEQ ID NO 14
<211> LENGTH: 30
<212> TYPE: DNA
<213> ORGANISM: Artificial Sequence
<220> FEATURE:
<223> OTHER INFORMATION: primer

<400> SEQUENCE: 14

caatatttta aagccttaag aaactttgtg                                    30


<210> SEQ ID NO 15
<211> LENGTH: 30
<212> TYPE: DNA
<213> ORGANISM: Artificial Sequence
<220> FEATURE:
<223> OTHER INFORMATION: primer

<400> SEQUENCE: 15

caatatttta aagccttaag gggggcggt                                     30
```

FULL-LENGTH INFECTIOUS CDNA CLONES OF TICK BORNE FLAVIVIRUS

CROSS-REFERENCE TO RELATED APPLICATIONS

This application is a continuation of international application number PCT/US01/04460, and claims the benefit of priority of international application number PCT/US01/04460 having international filing date of Feb. 9, 2001, designating the United States of America and published in English, which claims the benefit of priority of U.S. provisional patent application No. 60/181,490, filed Feb. 10, 2000; both of which are hereby expressly incorporated by reference in their entireties.

FIELD OF THE INVENTION

The present invention relates to the field of virology. Embodiments described herein include cDNA clones of the Langat tick-borne flavivirus.

BACKGROUND OF THE INVENTION

There are more than 60 antigenically related, positive strand RNA viruses in the arthropod-borne flavivirus genus of the family Flaviviridae, many of which are important human pathogens. The antigenically-related tick-borne encephalitis virus complex of the flavivirus family includes tick-borne encephalitis virus (TBEV, formerly called Russian spring-summer encephalitis virus), Kyassanur forest disease, Langat, Louping ill, Negishi, Omsk hemorrhagic fever, and Powassan viruses (Calisher, C. H., Karabatsos, N., Datrymple, J. M., Shope, R. E., Porterfield, J., Westaway, E. G., and Brant, W. E. (1989) Antigenic relationships between flaviviruses are determined by cross-neutralization test with polyclonal antisera. J. Gen. Virol., 70, 27–43.; Monath , T. P., and Heinz, F. X. (1996) Flaviviruses. In "Fields Virology." (B. N. Fields, D. M. Knipe & P. M. Howley, Eds.), 3$^{rd}$ ed., pp. 961–1035. Lippincott-Raven Publishers, Philadelphia & New York.). These viruses are endemic throughout most of the Northern Hemisphere, and except for Langat, cause human disease of varying severity that can have mortality as high as 20 to 30%. Tick-borne encephalitis remains a pressing public health problem in Eastern Europe and Russia, where 9,000–12,000 patients are diagnosed annually. A significant increase in mortality was recorded in 1956 and 1964, when morbidity reached 4,500–4,600 per 100,000 persons (Gaidamovich, S. Y. (1995) Tick-borne flavivirus infections. In "Exotic Viral Infections." (J. S. Porterfield, Ed.) pp. 203–221. Chapman & Hall, London.).

The tick-borne encephalitis flaviviruses share envelope glycoprotein epitopes that often induce cross-resistance among viruses of the group. Approximately three decades ago, these properties of antigenic cross reactivity and the subsequent recognition of virulence polymorphism suggested that successful immunization might be achieved using a live, naturally attenuated tick-borne flavivirus (Il'enko, V. I., Smorodincev, A. A., Prozorova, I. N., and Platonov, V. G. (1968) Experience in the study of a live vaccine made from the TP21 strain of Malayan Langat virus. Bull. W. H. O. 39, 425–431.; Price, W. H., Thind, I. S., Teasdall, R. D., and O'Leary, W. (1970) Vaccination of human volunteers against Russian spring-summer (RSS) virus complex with attenuated Langat E5 virus. Bull. W. H. O. 42, 89–94.; Mayer, V., Orolin, D., Pogady, J., Starek, M., Kubistova, K., Gajdo-Sova, E., and Buran, I. (1976) Experimental live tick-borne encephalitis vaccine (Langat E5"14"

virus clone): volunteers 1 and 2 years after single-dose immunization. Acta virol., 20, 215–225.). The impetus for this approach was the recovery of a virus from ticks in Malaysia, namely Langat virus (LGT), strain TP21, that did not appear to be associated with human disease under natural conditions (Gordon Smith, C. E. (1956) A virus resembling Russian spring-summer encephalitis virus from an Ixodid in Malaya. Nature (London) 178, 581–582.). Immunization of animals and human volunteers with LGT induced a high level of virus-neutralizing antibodies against various members of TBEV complex such as Powassan, Kyassanur forest disease and TBEV (Price, W. H., Thind, I. S., Teasdall, R. D., and O'Leary, W. (1970) Vaccination of human volunteers against Russian spring-summer (RSS) virus complex with attenuated Langat E5 virus. Bull. W. H. O. 42, 89–94.; Price, W. H., and Thind, I. S. (1973) Immunization of mice against Russian spring-summer virus complex and monkeys against Powassan virus with attenuated Langat E5 virus. Am. J. Trop. Med. Hyg. 22, 100–108.). Nonetheless, TP21 exhibited neurovirulence and neuroinvasiveness ("peripheral virulence") when tested in mice and therefore was considered too dangerous for use as a vaccine candidate. (Gordon Smith, C. E. (1956) A virus resembling Russian spring-summer encephalitis virus from an Ixodid in Malaya. Nature (London) 178, 581–582.; Thind, I. S., and Price, W. H. (1966a) A chick embryo attenuated strain (TP21 E5) of Langat virus. I. Virulence of the virus for mice and monkeys. Am. J. Epidemiol., 84, 193–213.; Pletnev, A. G., and Men, R. (1998) Attenuation of the Langat tick-borne flavivirus by chimerization with mosquito-borne flavivirus dengue type 4. Proc. Natl. Acad. Sci. USA, 95, 1746–1751.). Notwithstanding the direct neurovirulence measured by intracerebral inoculation observed for the TP21 Langat virus, its peripheral virulence (neuroinvasiveness) was significantly less than that of the very virulent Far Eastern strains of TBEV that produces human disease that has a 20 to 30% mortality. Several LGT strains, which were partially attenuated for mice and monkeys, were isolated and studied in the USA, Russia and Czechoslovakia (Nathanson, N., Thind, I. S., O'Leary, W., and Price, W. H. (1968) Histological studies of the monkey neurovirulence of group B arboviruses. IV. Evaluation of an attenuated strain (E5) of Langat virus. Am. J. Epidemiol. 88, 103–112.; Price, W. H., Thind, I. S., Teasdall, R. D., and O'Leary, W. (1970) Vaccination of human volunteers against Russian spring-summer (RSS) virus complex with attenuated Langat E5 virus. Bull. W. H. O. 42, 89–94.; Mayer, V., Orolin, D., Pogady, J., Starek, M., Kubistova, K., Gajdo-Sova, E., and Buran, I. (1976) Experimental live tick-borne encephalitis vaccine (Langat E5"14" virus clone): volunteers 1 and 2 years after single-dose immunization. Acta virol., 20, 215–225.; Smorodincev, A. A., and Dubov, A. V. (1986) Live vaccines against tick-borne encephalitis. In "Tick-Borne Encephalitis and Its Vaccine Prophylaxis", (A. A. Smorodincev, ed.), pp. 190–211. Meditsina, Leningrad.). One such strain, designated Yelantsev, was studied extensively in over 600,000 vaccinees in Russia as an experimental live vaccine against TBEV during the early 1970's (Smorodincev, A. A., and Dubov, A. V. (1986) Live vaccines against tick-borne encephalitis. In "Tick-Borne Encephalitis and Its Vaccine Prophylaxis", (A. A. Smorodincev, ed.), pp. 190–211. Meditsina, Leningrad.). Studies were discontinued when it was learned that vaccination was associated with a very low frequency of encephalitis, approximately one case per 20,000 immunizations. Nonetheless, this experience confirmed the initial view that LGT was highly attenuated and dearly the most benign member of the tick-borne flavivirus complex.

Shortly thereafter, a more attenuated mutant of LGT, designated strain E5, was selected by 42 passages in embryonated chicken eggs. LGT E5 exhibited less virulence for mice and monkeys than its TP21 parent. More recently, a study demonstrated that E5 exhibited less neurovirulence in mice than its TP21 parent (Pletnev, A. G., and Men, R. (1998) Attenuation of the Langat tick-borne flavivirus by chimerization with mosquito-borne flavivirus dengue type 4. Proc. Natl. Acad. Sci. USA, 95, 1746–1751.). Also, unlike its TP21 parent, E5 exhibited very little neuroinvasiveness and this was detectable only in a small fraction of mice inoculated peripherally with the largest amount of virus possible. Before considering the more attenuated E5 mutant of LGT as a possible candidate for use in prophylaxis of severe human disease caused by certain members of tick-borne flavivirus group, in the interest of safety scientists must reduce or ablate the last vestiges of virulence of LGT TP21 and E5 for mice by using a strategy that has been employed successfully in the past to attenuate dengue virus, namely the introduction of site-specific mutations into the full length infectious cDNA of the virus. Thus, there is a need for full length infectious cDNA clones of Langat.

Figures 1A, 1B, 1C:
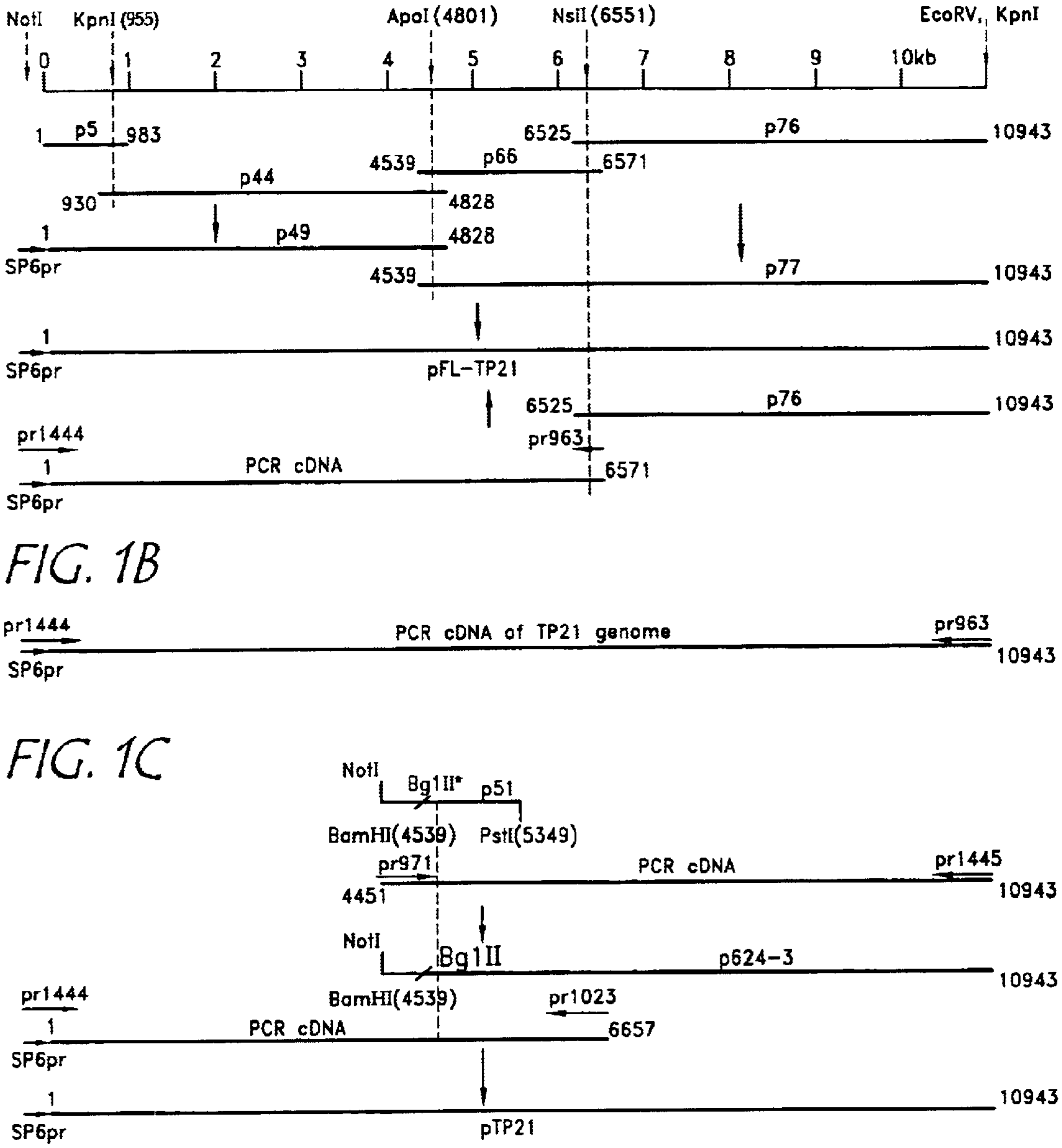
FIG. 1. Construction of full-length cDNA of LGT TP21 genome. (A). The assembly of full-length cDNA of TP21 in a plasmid was performed using the cDNA segments, which were cloned and sequenced as described earlier (Pletnev, A. G., and Men, R. (1998) Attenuation of the Langat tick-borne flavivirus by chimerization with mosquito-borne flavivirus dengue type 4. Proc. Natl. Acad. Sci. USA, 95, 1746–1751.) or were derived by long PCR. (B). Construction of full-length cDNA by a single long PCR. (C). The assembly of full-length cDNA from two cDNA segments of the genome that were derived from a low titered virus preparation ($3.8\times10^3$ PFU/ml). Position of the deavage site of NotI, KpnI, ApaI, NsiI and EcoRV in the cDNA shown in A or C by dashed lines. Solid lines indicate PCR cDNA fragments or cloned fragments of TP21 genome. Short horizontal arrows indicate position of SP6 promoter or position of primer; vertical solid arrows indicate subsequent steps in cloning strategy. The numbers at the ends of LGT cDNA fragments represent the first and the last nucleotide positions of the genome, respectively. NT numbering derived from the results of RT-PCR sequence of TP21. genome (Table 1). Note: *The junction of BglII and BamHI fragments in plasmid p51 or p624-3 eliminated both BglII and BamHI cleavage sites.

FIG. I. Construction of full-length cDNA of LGT E5 genome. (A). The assembly of full-length cDNA of E5 in a plasmid was performed using the pTP21-636 which was cloned and sequenced as described earlier and the SfiI(133)-AgeI(9737)-fragment that was derived by long PCR. (B). Construction and location of the deletions in the 3'-NCR of E5 genome. Position of the cleavage site of NotI, SfiI, AgeI, AflII, KpnI, and EcoRV in the cDNA shown in (A) or (B) by dashed lines. Solid lines indicate PCR cDNA fragments derived from the E5 genome. Short horizontal arrows indicate position of SP6 promoter or position of primer; vertical solid arrows indicate subsequent steps in cloning strategy. The numbers at the ends of LGT cDNA fragments represent the first and the last nucleotide positions of the genome, respectively. Nucleotide (nt) numbering derived from the results of RT-PCR sequence of E5 genome (GenBank accession no. AF253420). The position of the introduced deletion into the 3'-NCR, which extends from nt 10,379 to the position indicated on top of the striped boxes, are shown. (C). Sequence the 3'-NCR junctions of the deletion mutant cDNA genomes. The LGT E5 nucleotide sequence is in bold letters. The AflII cleavage site, which was used to generate deletions and TAA-stop codon indicated by the underlined sequence. The size of deletion, its position and corresponding plasmid construct is shown.

FIG. II. Analysis of growth of parental E5 and its recombinant derivative viruses in simian $LLCMK_2$ and Vero cells. Cells were infected with the indicated virus at MOI of 0.01 and following virus adsorption for 1 hr, inoculum was removed and fresh medium was added. Virus in culture medium was harvested at indicated times and its titer was determined by a focus-forming assay on the respective cells as described in Examples.

BRIEF DESCRIPTION OF THE TABLES

Table 1. Differences between the genomic sequence of LGT strains TP21 and E5 as determined by sequence analysis of fragments of virus genome initially cloned in *E. coli* or tested directly after derivation by RT-PCR.

Table 2. Sequence variation that occurred during the rescue of infectious LGT TP21 from plasmid cDNA.

Table 3. Neuroinvasiveness of parental LGT strains and cDNA-derived LGT TP21 virus clones in adult Swiss mice.

Table A. Mutations acquired when TP21/DEN4 and E5/DEN4 chimeras recovered in mosquito cells were adapted to grow efficiently in simian Vero cells.

Table B. Neuroinvasiveness of Vero cell grown LGT/DEN4 chimeras used for immunization.

Table C. Intraperitoneal (IP) immunization of inbred mice with low dose of Langat TP21/DEN4(vac) chimera protects against subsequent IP challenge with highly virulent TBEV strain Absettarov.

Table D. Intraperitoneal (IP) immunization of Swiss mice with Langat (LGT)/DEN4 chimeras protects against subsequent IP challenge with highly virulent TBEV strain Sofjin.

Table I. Changes from the consensus sequence of E5 that occurred during cloning, rescue of E5 from full-length cDNA and passage in simian Vero or chicken embryo fibroblast (CEF) cell culture.

Table II. Lineage and reduction of neuroinvasiveness of Langat virus (LGT) during passage in eggs and subsequent recovery from full-length cDNA and deletion of 320 nt from its 3'non-coding region.

Table III. Non-coding or coding changes in virus recovered from brain of moribund mice 14 or 28 days after IP inoculation of E5 or recombinant cDNA-derived E5 (clone E5-651 or clone E5-3'-320).

Table IV. Antibody response and protective efficacy of LGT virus strains in Swiss mice.

SUMMARY OF THE INVENTION

Infectious cDNA Clones of Langat Tick-borne Flavivirus that Differ from their Parent in Peripheral Neurovirulence Tick-borne flavivirus strain Langat TP21 (LGT TP21) recovered from ticks, is naturally attenuated for humans but retains demonstrable neurovirulence and peripheral virulence ("neuroinvasiveness") for mice. Previously, a mutant, strain E5, less virulent for mice was derived from LGT TP21. Multiple attempts to prepare a full-length infectious TP21 cDNA from cDNA fragments cloned in *E. coli* were uniformly unsuccessful. A more informative sequence than that obtained from these cloned cDNA fragments and similar E5 cDNA fragments was derived from RT-PCR fragments that had not been cloned in *E. coli*. Comparison of the RT-PCR consensus sequence of TP21 and E5 identified only 7 amino acid differences that might be responsible for the observed difference in virulence of these strains for mice. Eleven independent infectious cDNA clones of TP21 were recovered using two overlapping long RT-PCR fragments. Importantly, low titered virus used to prepare cDNA as template for PCR was harvested early in the growth cycle to minimize the frequency of deletion mutants that accumulated late in infection. The 4 analyzed rescued clones exhibited clone-specific minimal divergence from the consensus sequence but this limited variation was associated with diminished peripheral virulence for immunocompetent mice. Genetic manipulation of these clones will facilitate attenuation of LGT virulence and hasten the development of a safe and effective tick-borne flavivirus vaccine that will protect against viruses of the highly virulent tick-borne encephalitis virus complex.

Chimeric Langat/Dengue Viruses Protect Mice from Heterologous Challenge with the Highly Virulent Strains of Tick-borne Encephalitis Virus Langat virus (LGT), a tick-borne flavivirus, is naturally attenuated for humans but it is very virulent in SCID mice. In contrast, viable recombinant chimeras of LGT (preM and E genes) and dengue type 4 virus (all other sequences) recovered in mosquito cell culture were completely attenuated in SCID mice, but still capable of providing protection against LGT. In order to develop the chimeras into vaccine candidates we adapted them to replicate efficiently in simian Vero cells, a satisfactory substrate for human vaccines. The adapted chimeras remained completely attenuated for SCID mice and significantly, provided protection in immunocompetent mice against tick-borne encephalitis virus, the most virulent of the tick-borne flaviviruses.

Infectious cDNA Clone of Attenuated Langat Tick-borne Flavivirus (Strain E5) and a 3' Deletion Mutant Constructed from it Exhibit Decreased Neuroinvasiveness in Immunodeficient (SCID) Mice Forty-five years ago a naturally attenuated tick-borne flavivirus, Langat (LGT) strain TP21, was recovered from ticks in Malaysia. Subsequently, it was tested as a live attenuated vaccine for virulent tick-borne encephalitis viruses. In a large clinical trial its attenuation was confirmed but there was evidence of a low level of residual virulence. Thirty-five years ago further attenuation of LGT TP21 was achieved by multiple passages in eggs to yield mutant E5. In order to study the genetic determinants of the further attenuation exhibited by E5 and to allow us to manipulate the genome of this virus for the purpose of developing a satisfactory live attenuated tick-borne flavivirus vaccine, we recovered infectious E5 virus from a full-length cDNA clone. The recombinant E5 virus (clone 651) recovered from a full-length infectious cDNA clone was more attenuated in immunodeficient mice than that its biologically derived E5 parent. Increase in attenuation was associated with three amino acid substitutions, two located in the structural protein E and one in non-structural protein NS4B. Subsequently an even greater degree of attenuation was achieved by creating a viable 320 nucleotide deletion in the 3'-noncoding region of infectious full-length E5 cDNA. This deletion mutant was not cytopathic in simian Vero cells and it replicated to lower titer than its E5-651 parent. In addition, the E5 3' deletion mutant was less neuroinvasive in SCID mice than its E5-651 parent. Significantly, the deletion mutant proved to be 119,750 times less neuroinvasive in SCID mice than its progenitor, LGT strain TP21. Despite its high level of attenuation, the E5 3' deletion mutant remained highly immunogenic and IP inoculation of 10 PFU Induced complete protection in Swiss mice against subsequent challenge with 2,000 IP $LD_{50}$ of the wild-type LGT TP21.

DETAILED DESCRIPTION OF THE INVENTION

Infectious cDNA Clones of Langat Tick-borne Flavivirus that Differ from their Parent in Peripheral Neurovirulence Consensus sequences of TP21 and E5 genome. The complete nucleotide sequence of the wild type LGT virus (TP21 strain) genome and its more attenuated derivative, strain E5, recovered following multiple passages in chick embryo tissue, was determined previously from cDNA fragments cloned in *E. coli* (Pletnev, A. G., and Men, R. (1998) Attenuation of the Langat tick-borne flavivirus by chimerization with mosquito-borne flavivirus dengue type 4. Proc. Natl. Acad. Sci. USA, 95, 1746–1751.). Initial attempts to prepare infectious full-length cDNA clones of LGT TP21 from these cDNA fragments derived from RNA of a high titered virus suspension of TP21 were uniformly unsuccessful (FIG. 1, part A). Twelve stable individual full-length cDNAs were assembled in plasmids, but RNAs transcribed from these cDNA clones were not infectious for simian Vero or $LLCMK_2$ cell culture for reasons not understood at that time. It was possible that this was a result of spontaneous mutations in the LGT genome that had occurred during virus amplification in Vero cells or during amplification of full-length cDNA clones in the bacterial vector.

For this reason, it was decided to re-examine the sequence of the LGT genome by directly sequencing RT-PCR cDNA fragments without prior cloning in bacteria. Four overlapping cDNA fragments representing the full-length genome of TP21 or E5 virus were produced using high fidelity PCR, and the sequence of these overlapping fragments was determined. The sequence of each virus was determined twice, once with fragments that were derived from a virus suspension with a titer of $3.8\times10^3$ PFU/ml (TP21) or $1.2\times10^4$ PFU/ml (E5) and once with fragments derived from a virus suspension that was harvested one day later and titered $2.2\times10^6$ PFU/ml (TP21) or $4.0\times10^6$ PFU/ml (E5). Consensus sequences of both LGT strain genomes were found to differ from the previously published sequences determined from cDNA fragments cloned in *E. coli* (Table 1). The TP21 and E5 genomes were both 10,943 nucleotides (nt) in length and contained a 130 nt 5 non-coding region and a 568 nt 3' non-coding region. The sequence of the 5' termini of both LGT strains was identical. This was also the case for the 3' termini. The consensus sequences of TP21 and E5 derived by RT-PCR were thought to be more informative for identifying strain-specific mutations that might be responsible for differences in biological characteristics than were sequences derived from single DNA fragments cloned in *E. coli.*

There were 12 nucleotide differences in the consensus sequence of the two LGT strains (TP21 and E5), of which 7 produced an amino acid substitution in the envelope structural protein E or nonstructural protein NS3 or NS5 (Table 1). Among the seven amino acid changes in RT-PCR consensus sequence of TP21 and E5, four amino acid differences ($Asn_{389}$ to Asp in E, $Asn_{22}$ to Ser, $Phe_{248}$ to Tyr and $Phe_{317}$ to Leu in NS3) were also observed previously when TP21 and E5 cDNA fragments were cloned in *E. coli* (Pletnev, A. G., and Men, R. (1998) Attenuation of the Langat tick-borne flavivirus by chimerization with mosquito-borne flavivirus dengue type 4. Proc. Natl. Acad. Sci. USA, 95, 1746–1751.). Three additional amino acid substitutions ($Phe_{119}$ to Val in E protein and $Ser_{422}$ to Thr and $Arg_{542}$ to Lys in NSS protein) were identified in the consensus sequence determined from RT-PCR fragments of TP21 and E5. Another six amino acid differences, which were previously detected in the sequence of cloned fragments of TP21 and E5 (Pletnev, A. G., and Men, R. (1998) Attenuation of the Langat tick-borne flavivirus by chimerization with mosquito-borne flavivirus dengue type 4. Proc. Natl. Acad. Sci. USA, 95, 1746–1751.), were not found in RT-PCR consensus sequences. The somewhat greater variability observed with the cloned cDNA probably reflects bacterial selection during the cloning procedure and/or sequence heterogeneity in the viral RNA's that were employed for cDNA doning in *E. coli.*

Figure 2:
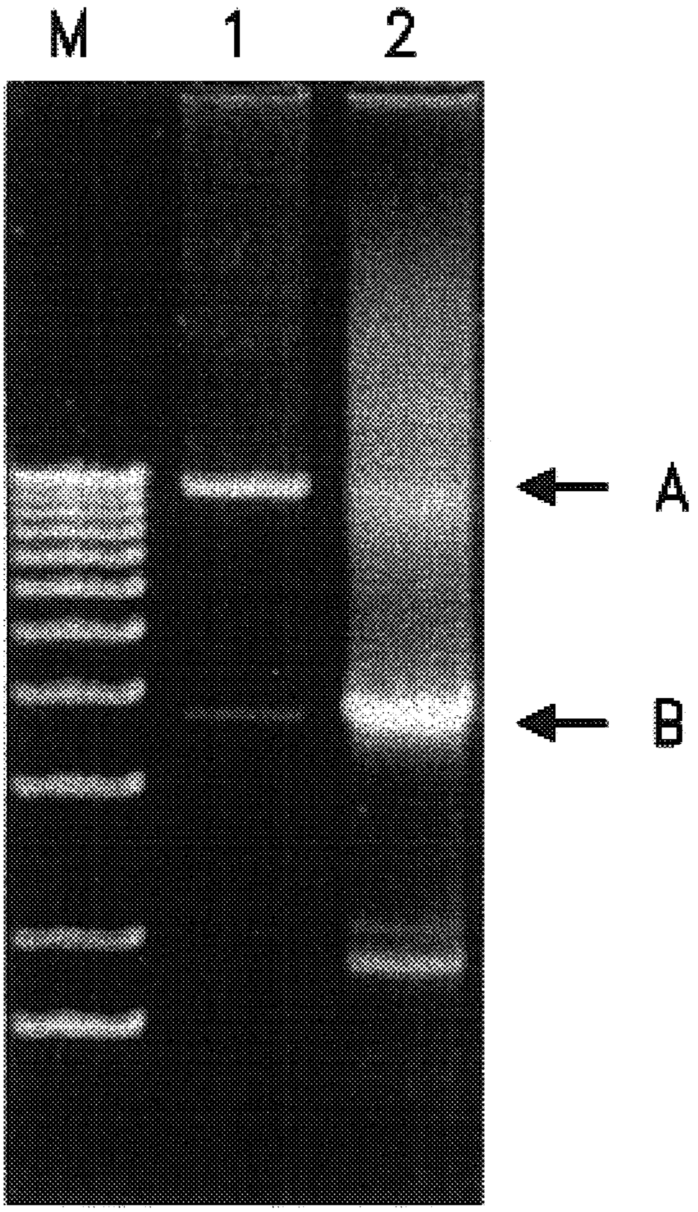
FIG. 2. Analysis of PCR-amplified cDNA from TP21 genome by 0.7% agarose gel electrophoresis. RT-PCR products were synthesized using RNA of TP21 virus which was isolated from low titered virus (lane 1; titer of $3.8\times10^3$ PFU/ml on Vero cells) or high titered virus (lane 2; titer of $2.4\times10^9$ PFU/ml on same cell line). PCR was performed using oligos 1444 and 1445 as primers under conditions described in Examples, and 10 $\mu l$ of reaction mixture was loaded on gel. Fragments of approximately 11 kb in length (band A) represent complete or nearly compete full-length genome cDNA. It was isolated from the gel and used for transcription of RNAs that were then used for transfection of Vero cells in culture. Shorter fragments approximately 4 kb in length (band B) were sequenced after extraction from gel. Molecular weight markers are displayed in lane M. The next to the top marker corresponds to 11 kb.

Infectious full-length TP21 cDNA. Having failed to assemble an infectious cDNA of the TP21 genome in bacteria (FIG. 1, part A), we attempted to circumvent the difficulties associated with cloning cDNA in a bacterial vector by preparing infectious full-length cDNA using long PCR. Also, we investigated the possibility that spontaneous mutations of the LGT genome might be greater for virus that attained a high titer during extended growth in cell culture. Full-length cDNA of TP21 virus was produced (FIG. 1, part B and FIG. 2) when high fidelity PCR was performed using a positive-sense primer that contained SP6 polymerase promoter immediately upstream of the first 22 nts of LGT sequence, and a negative-sense primer that was complementary to the LGT nts 10,921–10,943 of the 3' terminus. The latter primer contained an EcoRV cleavage site immediately following the 3' end sequence. As shown in FIG. 2, the dominant PCR product 1A (lane 1, band A) derived from low titered virus ($3.8\times10^3$ PFU/ml) was approximately 11 kb in length. In contrast, the PCR product 2A (lane 2, band A) derived from high titered virus ($2.4\times10^9$ PFU/ml) contained very little full-length cDNA, while the major product was considerably shorter, approximately 4 kb in length (lane 2, band B). Sequence analysis indicated that this fragment (lane 1 or 2, band B) represented a truncated LGT genome extending from nt 1 to 3779 that was joined to the last 23 nts of the 3' end of genome present in the negative-sense primer (oligo 1445), which was used for RT and PCR. It should be noted here that the last seven nucleotides at the 3' end of oligo 1445 were also complementary to the LGT genome sequence at nucleotide positions 3780 to 3786. It is possible that the shorter products (lane 1 or 2, band B) were produced by the binding of the primer to this alternative site on the viral genome during amplification by RT-PCR rather than to an altered 3' terminal sequence selected for by high multiplicity passage.

The approximately full-length RT-PCR cDNA fragments (band A, lane 1 or 2; FIG. 2) were digested with EcoRV, and RNA transcripts from these templates were tested for infectivity in Vero cells. Evidence of infection in Vero cells was detected by immunofluorescence assay (IFA) on day 12 using LGT-specific antibodies. At that time, 80–90% of cells transfected with RNA from PCR product 1A were positive, while only a few IFA-positive cells were observed when RNA transcripts from PCR product 2A were used. This indicated that infectious cDNA was recovered most effectively when low titered virus suspension was used as a source of full-length cDNA of the genome. This probably reflects alteration in the viral RNA genome that occurs with higher frequency during the more prolonged period of virus replication required to achieving a high titer. For this reason, viral RNA from a low titered TP21 virus suspension harvested two days post-infection was used for construction of full-length TP21 cDNA.

Recovery of LGT viruses from cloned cDNA and their characterization. Two overlapping cDNA fragments (FIG. 1, part C) were prepared by long PCR using RT product derived from RNA of low titered TP21 virus stock ($3.8\times10^3$ PFU/ml). The PCR product (approximately 6.1 kb) representing the 3' region of the genome was cloned in bacterial vector p5'-2(NotI, XhoI, ΔHindIII) in two steps as described in the Examples and illustrated in FIG. 1 (Part C). The resulting clone p624-3 that contained LGT nts from 4539 to the end of genome was selected based on restriction enzyme analysis. Subsequently, the remaining 5' sequence of TP21 genome (approximately 4.8 kb) together with the SP6 promoter, present at the 5' end immediately upstream of the LGT sequence, was generated by long PCR and ligated into the NotI and ApaI digested p624-3 plasmid. Cloning of this construct in *E. coli* yielded twenty-eight stable full-length LGT TP21 cDNA clones. However, some polymorphism was observed among the stable full-length LGT cDNAs with respect to restriction enzyme digestion pattern. The sequence of four of the plasmids (pTP21-636, pTP21-649, pTP21-656 and pTP21-689) was analyzed and was found to conform very dosely to the consensus sequence of TP21.

Prior to producing run-off transcripts, the plasmid DNA template was linearized at the EcoRV cleavage site that is present three nucleotides downstream of the 3' end of LGT TP21 sequence. As a consequence, the RNA transcripts contained three additional nucleotides GAU at the 3' terminus as well as an additional G residue at the 5' terminus. Full-length RNA generated by SP6 polymerase from 28 different plasmids was tested for infectivity by transfection of hamster BHK, or simian Vero or $LLCMK_2$ cells. Eleven individual LGT TP21 cDNA clones were infectious. Evidence of virus infection was detected by IFA with LGT-specific hyperimmune mouse ascitic fluid (HMAF) in 80–100% of transfected cells on day 5. Additional evidence that the recovered viruses were LGT was provided by comparison of LGT-specific proteins which were produced by parental TP21 or its progeny cDNA viruses in infected BHK, Vero or $LLCMK_2$ cells as demonstrated by immunoprecipitation assay with LGT-specific HMAF or monoclonal antibodies. The specific infectivities of RNA transcripts that were derived from three different cDNA clones ranged from $8\times10^3$ to $2\times10^5$ PFU/μg. This was significantly less than the infectivity of TP21 virion RNA which was $4\times10^6$ PFU/μg measured on Vero cells under same experimental conditions. Stock preparations of rescued TP21 clones were produced by passaging the virus in Vero cells and harvesting the supernatant medium of infected cultures. Virus titer of four rescued TP21 clones: TP21-636, TP21-649, TP21-656 and TP21-689 (designated 636, 649, 656 and 689) measured by plaque assay on $LLCMK_2$ cells varied from $1.2\times10^7$ to $2.4\times10^8$ PFU/ml 7 days post-infection.

The rescued cDNA-derived LGT clones produced characteristic LGT TP21 plaques 3.5 mm in diameter on $LLCMK_2$ cells 7 days post-infection, except for 649 virus that produced small plaques with an average diameter of 0.8 mm. Virus replication was further analyzed by monitoring the virus titer on days 0, 1, 2, 3, 4 and 5 after infection of Vero cells. Significant differences were not observed between the growth of recovered LGT clones and their parental virus.

Nucleotide sequence analysis of recovered viruses. The four viruses recovered from the transfection of Vero cells (i.e., clones 636, 649, 656 and 689) were amplified by further passage in Vero cells, and virion RNA was used for RT-PCR. Subsequent sequencing of the complete genome of rescued virus was performed using four overlapping PCR fragments without prior cloning in *E. coli*. Mutations in RNA viruses such as LGT can accumulate during RT-PCR, bacterial cloning of a cDNA genome and/or during adaptation and propagation of virus in cell culture. To gain a better understanding of the source of genetic variability of the newly recovered LGT viruses: (i) sequence analysis of the 5' half of the genome (nts 1–5300) of each rescued virus was performed twice in independent experiments in which virus was grown, viral RNA isolated and subjected to RT-PCR; the 3' half of the viral genome was sequenced in a similar manner but only once; and (ii) the nucleotide sequence of the viral insert in each of the four plasmids, from which-infectious RNA transcripts were derived, was also determined.

Analysis of the four selected infectious clones of TP21 revealed six differences in amino acid sequence from the consensus sequence of E5 previously determined by RT-PCR of its genome fragments (Table 1). These differences were observed at positions: 119 and 389 of E; 22, 248 and 317 of NS3 and 542 of NS5. Thus, the four rescued clones contained the TP21 consensus sequence in 6 of the 7 positions at which TP21 differed from its E5 derivative. Each infectious clone had Thr at position 422 of NS5, similar to E5, instead of the Ser residue of TP21 NS5 (Table 1).

There were three conserved nucleotide changes identified in the 3' half of the genome of each of these four recovered viruses not shown in Table 1. First, a change of $A_{10,436}\rightarrow G$ occurred in the 3' non-coding region, and the other two changes were found in nonstructural protein genes NS3 ($A_{5357}\rightarrow G$) and NS5 ($G_{9734}\rightarrow A$), which caused the substitution $Thr_{254}\rightarrow Ala$ in the NS3 protein and substitution $Asp_{691}\rightarrow Asn$ in the NSS protein. Nucleotide residues $G_{5357}$, $A_{9734}$ and $G_{10,436}$ present in the genome of the recovered viruses were also found in the plasmid DNA from which each of the viruses was derived and in the intermediate construct, plasmid p624-3. This suggests that these changes occurred during cloning in *E. coli* and were advantageous for amplification of plasmids containing LGT sequences or these differences might reflect the "quasispecies" of a positive strand RNA virus. In support of the latter explanation it should be noted that nucleotide variability G/A at position 9734 or position 10,436 had been observed in the consensus sequence of TP21 RT-PCR genome derived from high titered virus stock.

Sequence analysis also identified the presence of a few additional unique differences from the TP21 consensus sequence in the 5' half of the genome of each of the 4 rescued clones (Table 2). Fourteen of the 18 nucleotide differences from the consensus sequence of TP21 were also present in the plasmid DNA from which the 4 clones were derived. This provided evidence that the clones were indeed derived from cDNA. Of the total of 18 nucleotide differences observed between the consensus sequence of TP21 and the sequence of the four rescued virus genomes, 10 produced an amino add substitution in structural protein preM or E or in the nonstructural protein NS2A or NS2B. At least three nucleotide changes ($C_{4299}\rightarrow U$ in clones 636 and 689; $A_{590}\rightarrow G$ and $C_{4429}\rightarrow U$ in clone 656 underlined in Table 2) occurred during RNA transcription and transfection of Vero cells, or propagation of virus in cell culture, because these mutations were not present in the plasmid DNA templates from which these viruses were derived.

Clone 636 exhibited three nucleotide differences from the TP21 consensus sequence, only two of which resulted in an amino add change. A substitution $His_{438}$ to Tyr located near the transmembrane region of envelope protein E occurred at a position that is highly conserved among all mosquito-borne and tick-borne flaviviruses (Pletnev, A. G., Yamshchikov, V. F., and Blinov, V. M. (1990) Nucleotide sequence of the genome and complete amino add sequence of the polyprotein of tick-borne encephalitis virus. Virology 174, 250–263.; Gritsun, T. S., Holmes, E. C., and Gould, E. A. (1995) Analysis of flavivirus envelope proteins reveals variable domains that reflect their antigenicity and may determine their pathogenesis. Virus Research 35, 307–321.). Another amino add change, $Ala_{32}\rightarrow Val$ in the non-structural protein NS2B was also present in a significant proportion of virions of clone 689.

Clone 649 was more distinct from parental TP21 virus than the other viruses, because its virus genome contained 7 nucleotide differences (Table 2). Three of these mutations were silent while the other four caused an amino acid substitution in NS2A or NS2B protein. Possibly these unique mutations were responsible for 4-fold reduction in plaque size of 649 clone on $LLCMK_2$ cells compared to the parental TP21 and the other rescued viruses. It is interesting that clones 649 and 689 shared three common nucleotide changes at positions 2230, 3001 and 3599. One of these mutations caused the replacement of $Pro_{29}$ in the N-terminal region of NS2A protein by a Ser residue that is conserved among the TBEV-complex viruses (Pletnev, A. G., Yamshchikov, V. F., and Blinov, V. M. (1990) Nucleotide sequence of the genome and complete amino acid sequence of the polyprotein of tick-borne encephalitis virus. Virology 174, 250–263.).

An amino acid substitution in structural proteins preM ($Met_{38}\rightarrow Val$) and E ($Asp_{308}\rightarrow Ala$) as well as two silent mutations were identified in clone 656. Since the three-dimensional structure and function of the N-terminal part of preM protein is not known, the role of $Met_{38}\rightarrow Val$ change in preM protein is difficult to assess. Substitution of Asp→Ala at position 308 occurred in domain III of the E protein, which has been proposed to play a role in neurovirulence of tick-borne and mosquito-borne flaviviruses in mice (Rey, F. A., Heinz, F. X., Mandl, C., Kunz, C., and Harrison, S. C. (1995) The envelope glycoprotein from tick-borne encephalitis virus at 2 Å resolution. Nature 375, 291–298.; McMinn, P. C. (1997) The molecular basis of virulence of the encephalitogenic flaviviruses. J. Gen. Virol., 78, 2711–2722.). Also, it was observed earlier that Louping ill virus, a TBEV-complex flavivirus, exhibited decreased neuroinvasiveness in mice following a single amino acid substitution Asp→Asn in E protein at position 308 (Jiang, W. R., Lowe, A., Higgs, S., Reid, H., and Gould, E. A. (1993) Single amino acid codon changes detected in louping ill virus antibody-resistant mutants with reduced neurovirulence. J. Gen. Virol., 74, 931–935.). Thus, clone 656 of LGT may offer another opportunity to investigate the effect of mutation (Asp→Ala) at position 308 of E on neuroinvasiveness in mice.

Evaluation of cDNA-derived viruses in mice. Mice were employed as an experimental model to compare recovered LGT clones and their parental virus with respect to level of neuroinvasiveness, i.e. the capacity of virus to spread from peripheral site to central nervous system and cause encephalitis. Initially, adult outbred Swiss mice were injected intraperitoneally (IP) with $10^4$ or $10^6$ PFU of each virus and mortality was recorded for 28 days (Table 3). Previously wild-type LGT TP21 strain was shown to be virulent for 3-week-old Swiss mice with an intraperitoneal $LD_{50}$ of $10^{3.7}$ PFU (Pletnev, A. G., and Men, R. (1998) Attenuation of the Langat tick-borne flavivirus by chimerization with mosquito-borne flavivirus dengue type 4. Proc. Natl. Acad. Sci. USA, 95, 1746–1751.). Two clones, 649 and 689 virus, exhibited lower peripheral virulence than their LGT TP21 parent because only 12.5% or 40%, respectively, of adult mice inoculated IP with 200 $LD_{50}$ ($10^6$ PFU) developed symptoms of encephalitis and died. Death did not occur when mice were inoculated with $10^4$ PFU of 649 virus. These two viruses shared only one common amino acid change $Pro_{29}$ to Ser in NS2A protein, which might be associated with reduced peripheral neurovirulence of these rescued viruses in normal mice. The remaining two rescued clones, 636 and 656 virus, together with the attenuated LGT E5 strain were even more attenuated than parental LGT TP21 with respect to neuroinvasiveness. This indicates that these clones and LGT E5 were at least 200-fold less neuroinvasive in normal immunocompetent mice than their LGT TP21 parent.

Figure 3:
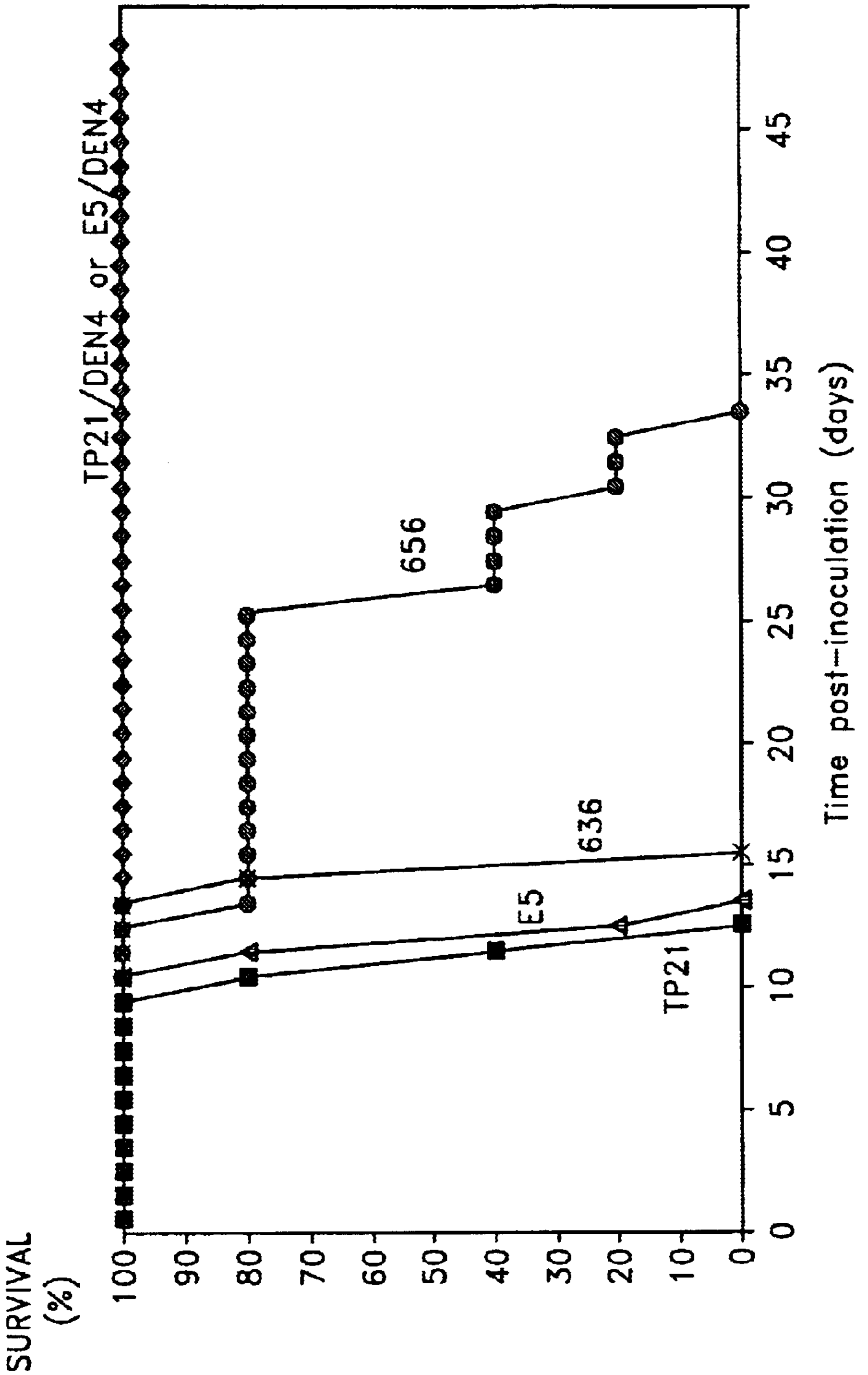
FIG. 3. Test for neuroinvasiveness of two infectious cDNA-derived clones of LGT TP21 in SCID mice. Comparison of mortality following intraperitoneal (IP) inoculation of $10^2$ PFU of clone 636 or 656 with that of the uncloned TP21 parental virus and its more attenuated E5 derivative. The previously described TP21/DEN4 and E5/DEN4 chimeras infectious for normal mice, served as virus controls that were fully attenuated in SCID mice. For this reason the chimeras were inoculated IP with a higher dose (i.e., $10^5$ PFU).
Figures 4, 4A, 4B:
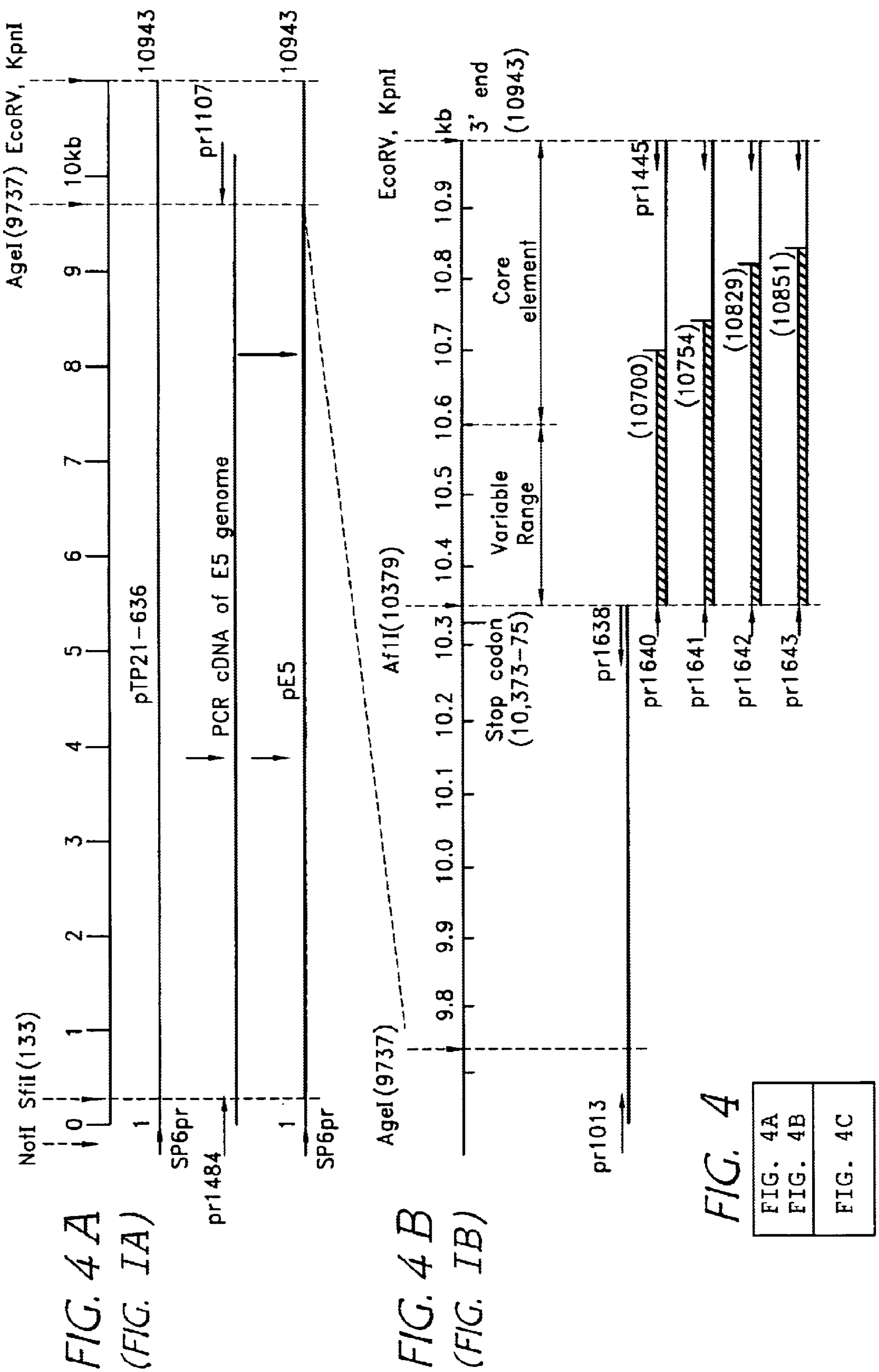
Figure 5:
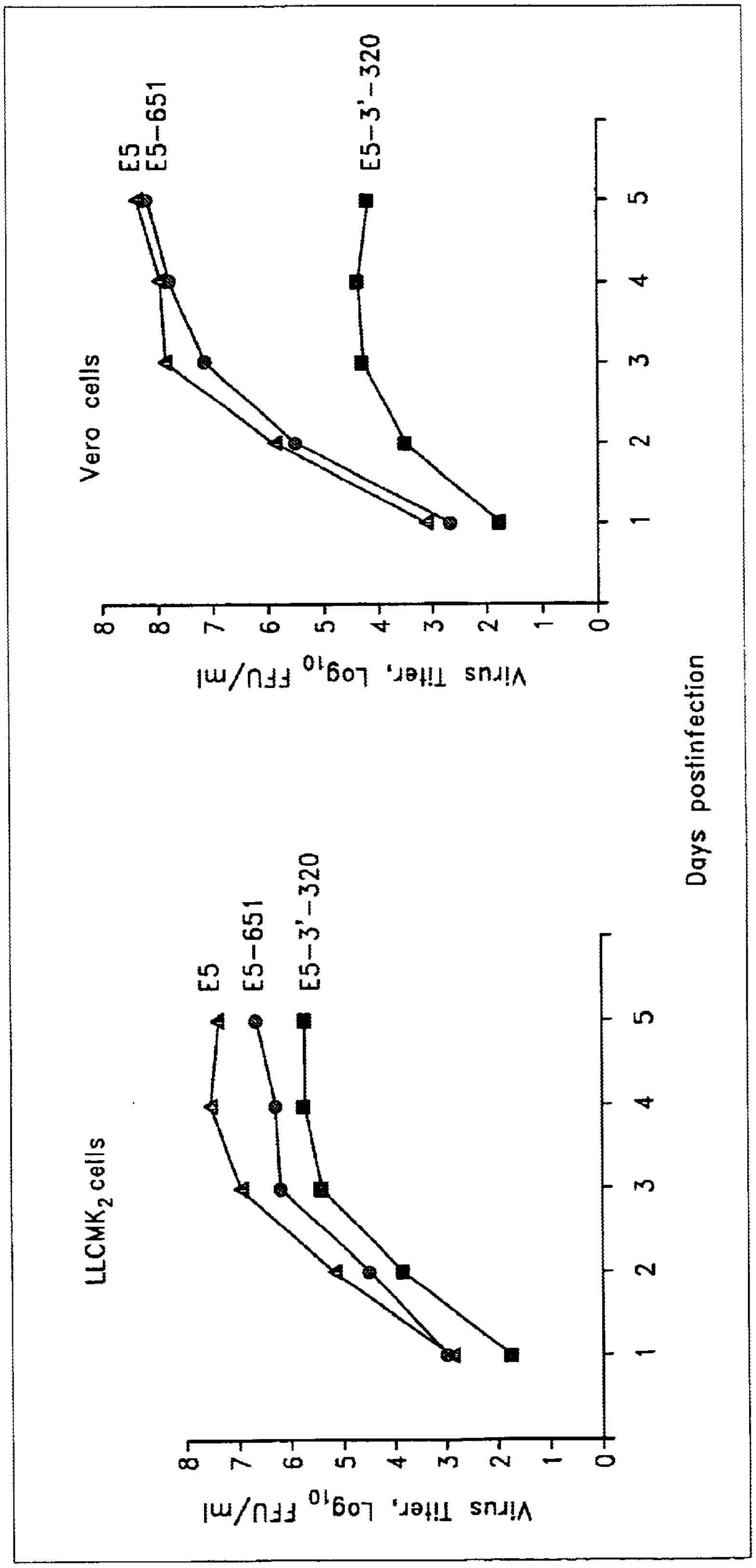

In an earlier study (Pletnev, A. G., and Men, R. (1998) Attenuation of the Langat tick-borne flavivirus by chimerization with mosquito-borne flavivirus dengue type 4. Proc. Natl. Acad. Sci. USA, 95, 1746–1751.), the attenuated E5 strain derived from TP21 exhibited peripheral neurovirulence in adult mice only when the amount of virus inoculated was increased to $10^7$ PFU or when a more sensitive test system, such as SCID mice, was used to measure neuroinvasiveness. To evaluate neurovasiveness of the more attenuated rescued viruses (clones 636 and 656), SCID mice, that are at least $10^6$ times more sensitive than normal mice for detection of peripheral neurovirulence, were inoculated IP with $10^2$ PFU (FIG. 3) (Pletnev, A. G., and Men, R. (1998) Attenuation of the Langat tick-borne flavivirus by chimerization with mosquito-borne flavivirus dengue type 4. Proc. Natl. Acad. Sci. USA, 95, 1746–1751.). Clone 636 did not appear to differ in neuroinvasiveness from its TP21 parent in SCID mice. Clone 656 also killed all inoculated mice during the observation period, but the survival time was increased at least two fold. The last 656-inoculated mouse died on day 34 post-infection, which was 21 days later than the last death of TP21-inoculated mice. This delay in death suggests that clone 656 replicated and spread more slowly in immunodeficient mice. For this reason this clone was studied in greater detail. Its $LD_{50}$ was evaluated by inoculating groups of 5 SCID mice IP with 1, 10 or 100 PFU. The $LD_{50}$ estimate obtained in this manner was 40 PFU. Thus, clone 656 was $10^4$ times less neuroinvasive than TP21 (estimated $LD_{50}$ for SCID mice of 0.004 PFU) and $6.6\times10^2$ times less pathogenic than E5, the attenuated TP21 derivative (estimated SCID mice $LD_{50}$ of 0.06 PFU) (Pletnev, A. G., and Men, R. (1998) Attenuation of the Langat tick-borne flavivirus by chimerization with mosquito-borne flavivirus dengue type 4. Proc. Natl. Acad. Sci. USA, 95, 1746–1751.). However, the level of attenuation of clone 656 was considerably less than that achieved by LGT/Dengue chimeric viruses (Pletnev, A. G., and Men, R. (1998) Attenuation of the Langat tick-borne flavivirus by chimerization with mosquito-borne flavivirus dengue type 4. Proc. Natl. Acad. Sci. USA, 95, 1746–1751.) as well as TBEV/DEN4 chimeras (Pletnev, A. G., Bray, M., Huggins, J., and Lai, C.-J. (1992) Construction and characterization of tick-borne encephalitis/dengue type 4 viruses. Proc. Natl. Acad. Sci. USA, 89, 10532–10536.; Pletnev, A. G., Bray, M., and Lai, C.-J. (1993) Chimeric tick-borne encephalitis and dengue type 4 viruses: effects of mutations on neurovirulence in mice. J. Virol., 67, 4956–4963.) (Dr. J. Huggins, USAMRIID, personal communication). The lack of detectable neuroinvasiveness of the TP21/DEN4 and E5/DEN4 chimeras for SCID mice was confirmed when mice inoculated IP with a dose of $10^5$ PFU survived the observation period (FIG. 3).

Sequence analysis of RT-PCR-produced cDNA fragments of the genome of wild type LGT TP21 strain and its attenuated derivative, strain E5, allowed for the identification of mutations that might be responsible for differences in peripheral neurovirulence of these strains in mice and monkeys as well as differences in growth rate in HeLa cells (Thind and Price, 1966a and 1966b; Nathanson et al., 1968; Price and Thind, 1973). Only 7 amino acid differences in the consensus sequences of the polyproteins of these strains were Identified (Table 1); four of these changes were observed previously when cDNA fragments of both strains of LGT were cloned in *E. coli* (Pletnev, A. G., and Men, R. (1998) Attenuation of the Langat tick-borne flavivirus by chimerization with mosquito-borne flavivirus dengue type 4. Proc. Natl. Acad. Sci. USA, 95, 1746–1751.). Only two of the seven amino acid differences ($Phe_{119}$ to Val and $Asn_{389}$ to Asp) were located in structural protein E. Mutation $Asn_{389}$ to Asp was located on the lateral surface of domain III of the E protein, and corresponds to a site at which mutation is thought to attenuate TBEV or Murray Valley encephalitis virus for mice (Rey, F. A., Heinz, F. X., Mandl, C., Kunz, C., and Harrison, S. C. (1995) The envelope glycoprotein from tick-borne encephalitis virus at 2 Å resolution. Nature 375, 291–298.; Monath , T. P., and Heinz, F. X. (1996) Flaviviruses. In "Fields Virology." (B. N. Fields, D. M. Knipe & P. M. Howley, Eds.), $3^{rd}$ ed., pp. 961–1035. Uppincott-Raven Publishers, Philadelphia & New York.; McMinn, P. C. (1997) The molecular basis of virulence of the encephalitogenic flaviviruses. J. Gen. Virol., 78, 2711–2722.).

Identification of one or more mutations responsible for the increased attenuation of LGT strain E5 compared with its parent, LGT strain TP21, can now be approached using reverse genetics. Our success in rescuing LGT TP21 from viral cDNA will allow for the investigation of the molecular basis for the observed difference in neuroinvasiveness of LGT TP21 and its tissue culture passage derivative, LGT E5, in mice and monkeys (Thind, I. S., and Price, W. H. (1966a) A chick embryo attenuated strain (TP21 E5) of Langat virus. I. Virulence of the virus for mice and monkeys. Am. J.

Epidemiol., 84, 193–213.; Thind, I. S., and Price, W. H. (1966b) A chick embryo attenuated strain (TP21 E5) of Langat virus. II. Stability after passage in various laboratory animals and tissue culture. Am. J. Epidemiol., 84, 214–224.; Nathanson, N., Thind, I. S., O'Leary, W., and Price, W. H. (1968) Histological studies of the monkey heurovirulence of group B arboviruses. IV. Evaluation of an attenuated strain (E5) of Langat virus. Am. J. Epidemiol. 88, 103–112.). Initially, attempts were made to construct full-length Infectious cDNA clones of TP21 from cDNA fragments that had been cloned previously in *E. coli* for the purpose of sequence analysis. RNA transcripts of full-length cDNA clones constructed from these DNA segments uniformly lacked infectivity. The failure of these full-length cDNAs to serve as a template for infectious RNA was probably a manifestation of deviation from the consensus sequence that was favored by the high titer of the virus used to clone cDNA in *E. coli* and the actual cloning procedure in this bacterium. This explanation is consistent with the 18 nucleotide differences (Table 1) that were identified between the sequence of the cloned cDNA fragments of TP21 genome derived from high titered virus stock and the consensus sequence of TP21 RT-PCR fragments that were not previously cloned in *E. coli* and that were derived from a low titered virus suspension that had been harvested early in its multicycle growth curve. To minimize the frequency of spontaneous mutation during virus preparation, a low titered TP21 virus suspension was used for construction of a full-length cDNA genome from long RT-PCR fragments. Success in generating infectious RNA from full-length cDNA of TP21 genome was achieved when this strategy was employed. Virus rescue was considerably more efficient when low titered virus ($3.8\times10^3$ PFU/ml) was used to prepare full-length cDNAs by long PCR than when high titered virus ($2.4\times10^9$ PFU/ml) was employed for this purpose. Subsequently, when full-length cDNA, derived from a low titered TP21 suspension, was constructed from two long overlapping RT-PCR fragments and cloned in *E. coli*, the RNA transcripts from 11 of the 28 stable cDNA clones were infectious in simian cell culture.

Three nucleotide changes ($C_{4299}$ to U in clones 636 and 689; $A_{590}$ to G and $C_{4429}$ to U in clone 656) were identified when the sequence of four of the rescued viruses was compared with the sequence of plasmid DNAs from which the four viruses were recovered. Presumably these 4 changes resulted from mutations that occurred during rescue of infectious virus from plasmid DNA. The remaining 14 nucleotide changes from the TP21 consensus sequence identified in the rescued viruses were also present in the plasmid DNA from which the 4 clones were derived (Table 2). This means that these mutations occurred earlier, i.e., prior to or during assembly of the RT-PCR fragments into full-length plasmid cDNA, possibly even as early as the spontaneous development of sequence polymorphism in the virus suspension ("quasispecies") used for RT-PCR amplification.

It should be noted that six of the 7 amino adds of the consensus sequence that differentiated LGT TP21 from its E5 derivative were retained in each of the rescued TP21 clones (Table 1), whereas the seventh TP21/E5 variant amino add ($Lys_{542}$ in NS5) conserved in each of the clones was that of E5.

The four rescued viruses contained the TP21/E5 consensus sequence (i.e., sequence common to both viruses, Table 1) with the exception that each of the 4 clones had three nucleotide changes ($A_{5357}$ to G, $G_{9734}$ to A, and $A_{10436}$ to G) which were also present in plasmid p624-3 and its derivatives, i.e., the full-length cDNA clones from which viruses were recovered. It is possible that these changes in each of the recovered viruses were responsible for the decreased peripheral neurovirulence observed in Swiss mice compared to parental TP21 virus. Clones 649 and 689 caused encephalitis and death in normal mice that were inoculated IP only when a large dose, $10^6$ PFU, was used (Table 3). It is interesting that both 649 and 689 virus did not differ from TP21 virus in the amino acid sequence of their structural proteins (Table 1 and 2), but these rescued viruses shared one common change $Pro_{29}$ to Ser in nonstructural NS2A protein. The presence of mutations in structural proteins of clones 636 and 656 was associated with a somewhat greater reduction of neuroinvasiveness in normal mice. Both of these rescued viruses lacked detectable neurovirulence when immunocompetent mice were inoculated IP with $10^6$ PFU. In contrast, when SCID mice were Inoculated IP, clone 636, which contained mutation $His_{438}$ to Tyr in E protein and $Ala_{32}$ to Val in NS2B protein, did not appear to differ from its TP21 parent in neuroinvasiveness for SCID mice; both viruses were highly neuroinvasive. Thus, these two mutations in clone 636 effected a decrease in neuroinvasiveness for normal mice, but did not ablate this property completely when tested in highly permissive SCID mice. During a previous study it was observed that SCID mice are $10^6$ to $10^7$ times more permissive than normal mice for detection of neuroinvasiveness (Pletnev, A. G., and Men, R. (1998) Attenuation of the Langat tick-borne flavivirus by chimerization with mosquito-borne flavivirus dengue type 4. Proc. Natl. Acad. Sci. USA, 95, 1746–1751.).

In SCID mice, clone 656 ($LD_{50}$ of 40 PFU) was $10^4$ times less neuroinvasive compared to parental TP21 virus ($LD_{50}$ of 0.004 PFU). However, when SCID mice were inoculated IP with $10^2$ PFU ($2.5LD_{50}$) of clone 656, mean survival time for mice increased two fold. Attenuation of clone 656 is probably the result of unique mutations in structural proteins ($Met_{38}$ to Val in preM and $Asp_{308}$ to Ala in E protein). A role for each of these substitutions in attenuation of LGT neuroinvasiveness is contemplated. It is of interest, that attenuation of another tick-borne flavivirus, Louping ill virus, was associated with single amino acid mutation in E protein at position 308 (Asp to Asn) or 310 (Ser to Pro) (Jiang, W. R., Lowe, A., Higgs, S., Reid, H., and Gould, E. A. (1993) Single amino acid codon changes detected in louping ill virus antibody-resistant mutants with reduced neurovirulence. J. Gen. Virol., 74, 931–935.). In addition, mutations, which were located at or near position 308 in E protein, and which had an effect on virulence of mosquito-borne flaviviruses were also observed in yellow fever virus and Japanese encephalitis virus (Schlesinger, J. J., Chapman, S., Nestorowicz, A., Rice, C. R., Ginocchio, T. E., and Chambers, T. J. (1996) Replication of yellow fever virus in the mouse central nervous system: comparison of neuroadapted and non-neuroadapted virus and partial sequence analysis of the neuroadapted strain. J. Gen. Virol., 77, 1277–1285.; Ni, H., and Barrett, A. D. T. (1998) Attenuation of Japanese encephalitis virus by selection of its mouse brain membrane receptor preparation escape variants. Virology 241, 30–36.; McMinn, P. C. (1997) The molecular basis of virulence of the encephalitogenic flaviviruses. J. Gen. Virol., 78, 2711–2722.). These findings taken together with the observation of demonstrable attenuation of clone 656 supports the hypothesis that this site plays an important role in virulence.

We also attempted to achieve greater attenuation of LGT by engineering two mutants of clone 656. The transfer of mutation $His_{438}$ to Tyr from clone 636 into the sequence of E protein of clone 656 to replace its corresponding sequence, compromised the infectivity of the resulting chimera. Infection by the chimeric 656/636 virus was initiated in 100% of RNA-transfected simian cells but infection did not proceed to maturation and release of infectious virus. The RNA transcripts from another construct, which contained the mutation $Pro_{29}$ to Ser in NS2A gene of clone 649 with remaining sequences derived from clone 656, generated viable virus in $LLCMK_2$ cells. A study in Swiss mice showed that this chimeric mutant, similar to its parent 656 virus, did not cause death or encephalitis when normal mice were inoculated IP with dose of $10^6$ PFU. Also, the two viruses did not differ when tested in SCID mice; both produced fatal encephalitis after a prolonged inoculation interval. This indicated that neuminvasiveness for SCID mice was not reduced when the mutations from clone 656 and the mutation in NS2A protein in clone 649 were combined in a single virus.

Finally, the 4 recovered viruses exhibited a spectrum of peripheral neurovirulence in mice probably due to the different pattern of mutations identified by sequence analysis of the rescued virus genomes. Two rescued viruses (649 and 689) exhibited moderately less neuroinvasiveness for immunocompetent adult Swiss mice compared to their parent TP21, while the remaining two clones (636 and 656) appeared to be neuroinvasive only in SCID mice. The 656 virus retained neuroinvasiveness for SCID mice but it appeared to be attenuated in these immunodeficient mice with respect to its TP21 parent or the E5 strain (Pletnev, A. G., and Men, R. (1998) Attenuation of the Langat tick-borne flavivirus by chimerization with mosquito-borne flavivirus dengue type 4. Proc. Natl. Acad. Sci. USA, 95, 1746–1751.). The attenuated E5 strain was initially selected from the TP21 strain by multiple passages in chick embryo cell culture as a potential live virus vaccine candidate to protect against illness caused by the members of TBEV complex (Price, W. H., Thind, I. S., Teasdall, R. D., and O'Leary, W. (1970) Vaccination of human volunteers against Russian spring-summer (RSS) virus complex with attenuated Langat E5 virus. Bull. W. H. O. 42, 89–94.). E5 exhibited reduced neurovirulence for monkeys, which was less than that of the 17D vaccine strain of yellow fever virus (Nathanson, N., Thind, I. S., O'Leary, W., and Price, W. H. (1968) Histological studies of the monkey neurovirulence of group B arboviruses. IV. Evaluation of an attenuated strain (E5) of Langat virus. Am. J. Epidemiol. 88, 103–112.). The availability of clone 656 infectious cDNA provides a foundation for further studies designed to remove the remaining vestige of neuroinvasiveness for immunodeficient mice as had been achieved previously by construction of Langat/Dengue chimeric viruses (Pletnev, A. G., and Men, R. (1998) Attenuation of the Langat tick-borne flavivirus by chimerization with mosquito-borne flavivirus dengue type 4. Proc. Natl. Acad. Sci. USA, 95, 1746–1751.).

Availability of infectious full length cDNA of Langat virus allows us to attenuate Langat virus by the introduction of site-specific attenuating mutations. This result permits us to construct attenuated mutants that are evaluated for attenuation and immunogenicity in adult volunteers. This success leads to the development of satisfactorily attenuated live virus vaccines for use in prevention of important tick-borne flavivirus disease.

Chimeric Langat/Dengue Viruses Protect Mice from Heterologous Challenge with Highly Virulent Strains of Tick-borne Encephalitis Characterization of Vero cell-passaged LGT/DEN4 chimeras. Two viable chimeric viruses that contained preM and E genes of wild-type LGT strain TP21 or its more attenuated derivative, LGT strain E5, with remaining sequences derived from DEN4 were recovered after transfection of mosquito C6/36 cells with full-length RNA transcripts of the full-length cDNA chimeric genome; however, infectious virus could not be recovered following transfection of simian cells (Pletnev, A. G., and Men, R. (1998). Attenuation of the Langat tick-borne flavivirus by chimerization with mosquito-borne flavivirus dengue type 4. Proc. Natl. Acad. Sci. USA 95, 1746–1751.). It should be noted that the former cells are considered to be unsuitable for preparation of human vaccines. Initially both TP21/DEN4 and E5/DEN4 chimeras recovered in mosquito cells were significantly reduced in effidency of viral replication and plaque formation in simian cells compared with parental TP21 or E5 virus as well as parental DEN4. However, it was possible to adapt the chimeric viruses to grow efficiently in certified Vero cells (W.H.O. Seed, 143 passage; Novavax, Inc., Rockville, Md.) suitable for use in production of human vaccines. This was accomplished by inoculating Vero cells with TP21/DEN4 or E5/DEN4 virus at a multiplicity of infection (MOI) of 1 or 5 and harvesting 2 to 4.5 mm virus plaques that developed after 10 days of incubation at 37° C. These plaque isolates were then subjected to four plaque to plaque passages in Vero cells in a successful attempt to select for virus that grew to higher titer, and produced plaques more efficiently. Seed stock of Vero cell culture-derived TP21/DEN4 or E5/DEN4 virus was prepared by passage of fourth plaque passage virus in Vero cells.

The Vero cell-adapted vaccine candidates (indicated as "vac") TP21/DEN4(vac) and E5/DEN4(vac) were then compared with each other and with their parental viruses with respect to neuroinvasiveness in mice, plaque morphology and maximum yield in simian and mosquito cells. The titer attained by the Vero cell-adapted TP21/DEN4(vac) and E5/DEN4(vac) chimeras was $4.6\times10^6$ PFU/ml and $3\times10^6$ PFU/ml in Vero cells and $1\times10^6$ PFU/ml and $3\times10^6$ PFU/ml in mosquito C6/36 cells, respectively, indicating parity had been achieved.

The increased cytopathic effect of the Vero cell-adapted chimeras in Vero cells suggested that host range mutations in the virus genome were selected during adaptation and propagation of these viruses in simian cells. For this reason a partial sequence of both chimeric virus genomes was determined by RT-PCR analysis of RNA extracted from purified virions to verify their chimeric structure and identify mutations that might play a role in Vero cell adaptation. Primer pairs (oligo 239 and oligo 442; see in (Pletnev, A. G., Bray, M., and Lai, C.-J. (1993). Chimeric tick-borne encephalitis and dengue type 4 viruses: effects of mutations on neurovirulence in mice. J. Virol. 67, 4956–4963.)) which amplify the DEN4 genome from nucleotide 18 to nucleotide 2832 were used to generate PCR products. Nucleotide sequence of the 5' noncoding region, the structural protein genes and nonstructural protein NS1 gene of each Vero cell culture-derived chimeric genome, including the C/preM and E/NS1 junctions, was determined and compared with the published sequence of the corresponding mosquito cell culture-derived chimeric virus genome (Table A) (Pletnev, A. G., and Men, R. (1998). Attenuation of the Langat tick-borne flavivirus by chimerization with mosquito-borne flavivirus dengue type 4. Proc. Natl. Acad. Sci. USA 95, 1746–1751.). Only three amino acid differences were identified and these were located in the preM and E protein sequence of the TP21/DEN4(vac) chimera that had been passaged 5 times in Vero cells following recovery in mosquito C6/36 cells. In a similar comparison, there were only 8 nucleotide differences in the sequence of the Vero cell-adapted E5/DEN4(vac) chimera, of which 6 produced an amino acid substitution and these were located in the envelope structural protein (E). The same amino acid substitutions in E at position 296 (Lys to Gln) and position 310 (Thr to Ala) were documented in the two chimeras. These shared mutations may play a role in alteration of cell tropism.

The change at nucleotide position 1437 of E5/DEN4(vac) genome results in an amino acid substitution of Ile for $Thr_{151}$ in a potential glycosylation site of E protein. Immunoprecipitation of viral E proteins from lysates of Vero cells infected with either a parental LGT virus or its chimeric virus indicated a difference in gel migration of the E protein of parental E5 virus and its chimeric E5/DEN4(vac) virus. The E protein of E5/DEN4 chimera migrated slightly faster than the E protein of E5 virus. This probably reflects loss of the one of the three potential N-linked glycosylation sites in E protein. In contrast, the gel mobility of E glycoprotein of TP21 and its chimeric TP21/DEN4(vac) virus did not differ.

Mouse neuroinvasiveness. In a previous study, LGT TP21 inoculated IP was only moderately attenuated for immunocompetent mice (Pletnev, A. G., and Men, R. (1998). Attenuation of the Langat tick-borne flavivirus by chimerization with mosquito-borne flavivirus dengue type 4. Proc. Natl. Acad. Sci. USA 95, 1746–1751.). In contrast, LGT E5 (an egg passage derivative of TP21), TP21/DEN4 and E5/DEN4 were completely attenuated when normal mice were inoculated by the IP route. However, the parental LGT viruses inoculated IP exhibited a very high level of virulence for SCID mice; the IP $LD_{50}$ was $4\times10^{-3}$ PFU for TP21 and $6\times10^{-2}$ PFU for E5 (Table B) (Pletnev, A. G., and Men, R. (1998). Attenuation of the Langat tick-borne flavivirus by chimerization with mosquito-borne flavivirus dengue type 4; Proc. Natl. Acad. Sci. USA 95, 1746–1751.). Significantly, this high level of virulence of the LGT strains for SCID mice was totally ablated when TP21 or E5 was used to construct a viable LGT/DEN4 chimera. In a previous study, the IP $LD_{50}$ in SCID mice for the two chimeras "rescued" and propagated in mosquito cells was $>10^7$ PFU (Pletnev, A. G., and Men, R. (1998). Attenuation of the Langat tick-borne flavivirus by chimerization with mosquito-borne flavivirus dengue type 4. Proc. Natl. Acad. Sci. USA 95, 1746–1751.). In the present study a similar analysis was performed for the Vero cell-adapted chimeras to determine if this level of attenuation for SCID mice had been retained after the chimeras were adapted to certified Vero cells that are qualified for use in the manufacture of a human vaccine.

Three-week-old Swiss mice and immunodeficient (SCID) mice (C.B.-17 ICR/scid/scid; Taconic Farms, Germantown, N.Y.) were used to assess virulence (Table B). At a dose of $10^5$ PFU delivered IP, parental TP21 caused 100% mortality in Swiss mice, whereas LGT E5, the TP21/DEN4(vac) chimera and the E5/DEN4(vac) chimera failed to cause fatal disease when inoculated IP at a dose of $10^5$ or $5\times10^5$ PFU. In addition, complete attenuation of both chimeric viruses was observed when SCID mice were inoculated IP. Although, TP21 or E5 virus produced 100% mortality when SCID mice were inoculated IP with $10^2$ PFU, neither mortality nor illness was observed when SCID mice were inoculated IP with $5\times10^5$ PFU of either LGT/DEN4 chimera. This indicates that Vero cell-adapted viruses, like their mosquito cell-grown parents, were significantly attenuated for mice under these conditions.

To determine if SCID mice that survived 7 weeks after IP inoculation with either LGT/DEN4 chimera were susceptible to challenge with parental TP21, surviving mice were inoculated IP with $10^2$ PFU of TP21. As expected all of these mice died between 10 and 13 days post-inoculation. Also, we were unable to recover infectious virus or detect viral RNA by PCR 50 days after IP inoculation of either highly attenuated chimera. Thus, we were unable to detect evidence of persistent infection.

Protection against challenge with virulent TBEV. The studies involving TBEV challenge were carried out in a biosafety level 4 laboratory at the Chumakov's Institute of Poliomyelitis and Viral Encephalitides, Moscow region, Russia or at the US Army Medical Research Institute of Infectious Diseases, Fort Detrick, Md., USA in accordance with procedures described in the Guide for the Care and Use of Laboratory Animals (National Institutes of Health, 1996).

Protection Induced by Immunization with a 600 PFU Dose of the TP21/DEN4 Chimera (Table C)

In the first experiment 6-week-old inbred CBA mice (14–20 g) in groups of 9 or 10 were inoculated IP with 600 PFU of TP21/DEN4(vac) once or twice with an interval of 29 days between inoculations. Immunized as well as non-immunized (control) mice were challenged IP on day 26 or 55 with 320 PFU ($32LD_{50}$) of the highly neuminvasive TBEV strain Absettarov, a European subtype virus (Ecker, M., Allison, S. L., Meixner, T., and Heinz, F. X. (1999). Sequence analysis and genetic classification of tick-borne encephalitis viruses from Europe and Asia. J. Gen. Virol. 80, 179–185.). The IP $LD_{50}$ of this strain for 14–20 g of CBA mice was estimated to be 10 PFU. Mice immunized with a single 600 PFU dose of the chimeric vaccine were only partially protected (60%) against $32LD_{50}$ of the virulent TBEV strain, whereas two inoculations of a 600 PFU dose of the chimera conferred complete protection against heterologous challenge with TBEV. In contrast, all 19 control CBA mice developed clinical signs consistent with lethal TBEV infection and died when challenged with TBEV.

During the second experiment a similar protocol was used to study the TP21/DEN4 chimera in BALB/c mice. Four-week-old BALB/c female mice (10–14 g) in groups of 5 or 10 were inoculated IP with 600 PFU of TP21/DEN4(vac) chimera one or more times with an interval of 26 to 66 days between inoculations (Table C). Mice were challenged IP at the indicated time with a dose of $320LD_{50}$ of TBEV strain Absettarov, whose IP $LD_{50}$ for 10–14 g BALB/c mice was estimated to be 1 PFU. In this experiment as well as the first experiment, non-immunized mice that served as controls were the same age as immunized mice to eliminate an effect of age-related resistance of mice to TBEV. All 40 non-immunized mice challenged with TBEV died with clinical signs of lethal TBEV infection. BALB/c mice inoculated with a single dose of the TP21/DEN4(vac) chimera were poorly protected against TBEV compared to CBA mice. However, protective efficacy increased when two or three doses of the chimeric vaccine strain were inoculated. Complete protection to TBEV challenge was achieved when the vaccine candidate was inoculated 4 times over period of 127 days.

Protection Induced by Inoculation of a $10^5$ PFU Dose of a Candidate LGr/DEN4 Vaccine (Table D)

Three-week-old outbred Swiss female mice (7–9 g) were inoculated by the IP route with: (i) $10^2$ PFU of LGT TP21 virus, LGT E5 virus or a cDNA-derived LGT TP21 virus (designated 656) or (ii) $10^5$ PFU of TP21/DEN4(vac), E5/DEN4(vac) or DEN4. When the candidate vaccine was administered twice, the second inoculation was given after an interval of 22 days. Eighteen days after the second immunization, all of the mice were bled to measure level of serum neutralizing antibodies against LGT TP21 virus, and six days later mice were challenged IP with a $100LD_{50}$ of the highly virulent strain Sofjin of TBEV, Far Eastern subtype (Clarke, D. H. (1964). Further studies on antigenic relationships among the viruses of the group B tick-borne complex. Bull. World Health Organ. 31, 45–56.). The 50% lethal dose of strain Sofjin for 8 weeks old mice was previously determined to be 0.5 PFU (Schmaljohn, C., Vanderzanden, L., Bray, M., Custer, D., Meyer, B., Li, D., Rossi, C., Fuller, D., Fuller, J., Haynes, J., and Huggins, J. (1997). Naked DNA vaccines expressing the prM and E genes of Russian spring summer encephalitis virus and Central European encephalitis virus protect mice from homologous and heterologous challenge. J. Virol. 71, 9563–9569.).

Previous studies in mice demonstrated a tight correlation between level of serum neutralizing antibodies to tick-borne flavivirus induced by immunization and resistance to challenge with homologous virus or other dosely related members of this group (Monath , T. P., and Heinz, F. X. (1996). Flaviviruses. In "Fields Virology." (B. N. Fields, D. M. Knipe and P. M. Howley, Eds.), $3^{rd}$ ed., pp.961–1035. Lippincott-Raven Publishers, Philadelphia/N.Y.; Price, W. H., and Thind, I. S. (1973). Immunization of mice against Russian spring-summer virus complex and monkeys against Powassan virus with attenuated Langat E5 virus. Am. J. Trop. Med. Hyg. 22, 100–108.; Schmaljohn, C., Vanderzanden, L., Bray, M., Custer, D., Meyer, B., Li, D., Rossi, C., Fuller, D., Fuller, J., Haynes, J., and Huggins, J. (1997). Naked DNA vaccines expressing the prM and E genes of Russian spring summer encephalitis virus and Central European encephalitis virus protect mice from homologous and heterologous challenge. J. Virol. 71, 9563–9569.). These earlier studies established that a close antigenic relationship existed between TBEV and LGT. Also, the sequence of the structural proteins preM and E of these flaviviruses is 85–88% homologous (Mandl, C. W., Iacono-Connors, L., Waliner, G., Holzmann, H., Kunz, C., and Heinz, F. X. (1991). Sequence of the genes encoding the structural proteins of the low-virulence tick-borne flaviviruses Langat TP21 and Yelantsev. Virology 185, 891–895.). Thus, we were not surprised to observe that the level of neutralizing antibodies measured against LGT TP21 virus showed a correlation with protective immunity to TBEV. In this experiment the LGT virus-specific immune response of mice was measured by determining the titer of serum LGT TP21 neutralizing antibodies induced by the chimeric vaccine candidate or its parental LGT virus. Individual serum samples were analyzed by a 50% focus reduction neutralization test (Okuno, Y., Fukunaga, T., Tadano, M., Okamoto, Y., Ohnishi, T., and Takagi, M. (1985). Rapid focus reduction neutralization test of Japanese encephalitis virus in microtiter system. Arch. Virol. 86, 129–135.; Ishimine, T., Tadano, M., Fukunaga, T., and Okuno, Y. (1987). An improved micromethod for infectivity assays and neutralization test of dengue viruses. Biken Journal 30, 39–44.) using TP21 virus (Table D). Mice inoculated once with $10^2$ PFU of TP21, TP21(656) or E5 virus or twice with $10^5$ PRU of the TP21/DEN4(vac) chimera developed a high level of neutralizing antibodies. against LGT TP21. In contrast, mice inoculated IP with $10^5$ PFU of DEN4 failed to develop TP21 neutralizing antibodies. Also, mice immunized with either chimeric virus once or E5/DEN4(vac) chimera twice developed a moderate level of TP21 serum neutralizing antibodies which was lower then observed previously (Pletnev, A. G., and Men, R. (1998). Attenuation of the Langat tick-borne flavivirus by chimerization with mosquito-borne flavivirus dengue type 4. Proc. Natl. Acad. Sci. USA 95, 1746–1751.), when the mosquito cell culture-derived chimeric viruses were used for immunization of outbred Swiss mice.

Mice previously inoculated with a low dose of E5 or TP21 were fully protected against subsequent TBEV challenge, whereas mice previously inoculated with DEN4 as well as non-immunized mice were not protected at all. This indicates that protection was due to a broad LGT immune response. Even a very low dose of live LGT virus (including the cDNA-derived TP21 virus) was highly effective in preventing disease caused by the antigenically related TBEV. Mice also became resistant to subsequent lethal challenge with Far Eastern subtype strain of TBEV after immunization with the chimeric viruses. The TP21/DEN4 (vac) appeared to be more immunogenic compared to E5/DEN4(vac) because mice inoculated with two doses of the former were fully protected against TBEV challenge. In contrast, only 67% of mice inoculated with two doses of E5/DEN4(vac) chimera survived lethal challenge by TBEV. Clearly, the parental LGT viruses were more immunogenic and protective than their DEN4 chimeras. However, it was possible to achieve greater safety and equivalent protective efficacy when the TP21/DEN4(vac) chimera was administered in a two-dose regime.

Consistent with the close antigenic relationship of LGT and TBEV, our studies with chimeric virus vaccine candidates in mice have shown a high degree of cross-protection between LGT and TBEV European subtype (strain Absettarov) or TBEV Far Eastern subtype (strain Sofjin). Thus, the LGT preM and E proteins of the chimeras represent effective protective antigens able to induce significant resistance to heterologous challenge with highly virulent TBEV. The encouraging results support the safety, immunogenicity and protective efficacy of candidate vaccine strains in mice as a model system.

Infectious cDNA Clone of Attenuated Langat Tick-borne Flavivirus (Strain E5) and a 3' Deletion Mutant Constructed from it Exhibit Decreased Neuroinvasiveness in Immunodeficient Mice Construction of full-length E5 cDNA clone and recovery of virus from cells transfected with full-length RNA transcripts. Earlier we succeeded in constructing stable LGT TP21 full-length cDNA clones from which infectious RNA could be transcribed in vitro. One of these full-length cDNA clones, plasmid pTP21-636, was used to create full-length cDNA of E5 genome by replacing almost the entire TP21 genome with the corresponding sequence of E5 strain. The complete nucleotide sequence of the wild type LGT virus (TP21 strain) genome and its more attenuated derivative, strain E5, was determined previously from cDNA fragments produced by RT-PCR (GenBank accession no. AF253419 and AF253420). The TP21 and E5 genomes were both 10,943 nucleotides (nt) in length and contained a 130 nt 5' non-coding region (NCR) and a 568 nt 3' NCR that were completely conserved. Twelve differences in genome sequence of TP21 and E5 strain were located between nucleotide positions 1325 and 9288. This region together with flanking conserved sequences (nts 133 to 1324 and nts 9289 to 9737) In the infectious cDNA of cloned full-length TP21 genome was targeted for substitution with the corresponding sequence of E5 (FIG. IA). An almost full-length cDNA fragment (approximately 10.5 kb) of the E5 genome was prepared by high-fidelity long PCR using an RT product derived from viral RNA extracted from a low titered E5 virus stock ($1.2\times10^4$ PFU/ml). Low titered virus harvested early in the growth cycle was used to prepare cDNA as template for PCR in order to minimize the presence of mutants with large 3' deletions or rearranged genomes that accumulate late in infection as observed earlier. Conservation of the 5' 132 nts and the 3' 1205 nts of TP21 and E5 allowed us to clone the PCR product of the E5 genome, spanning nts 133 to 9737, into the pTP21-636 vector replacing the corresponding TP21 sequence. Six stable full-length E5 cDNA clones were identified by restriction enzyme digestion pattern. The partial sequence of these plasmids (pE5) was analyzed and found to contain the E5-specific sequences that differentiate E5 from its TP21 parent.

Prior to producing run-off transcripts, the plasmid DNA template was linearized using EcoRV, whose deavage site is present three nucleotides downstream of the 3' end of LGT E5 sequence. Full-length RNA generated by SP6 polymerase from six different plasmids was tested for infectivity by transfection of chicken embryonic fibroblast (CEF) cells or simian Vero cells. Only one E5 cDNA clone (pE5-651) was infectious for both cell lines while the other clones were not viable. Evidence of virus infection was detected by IFA With LGT-specific HMAF. All of the transfected Vero cells and 20–30% of CEF-transfected cells were positive on day 5. Stock preparations of the rescued E5 clone were produced by passaging the virus once or twelve times in the cell line used for rescue and harvesting the supernatant medium of infected cultures. After one or 12 passages in Vero or CEF cells virus was analyzed for deviation of sequence from its biologically derived E5 parent.

Genetic variability of E5-651 virus during construction, recovery and passage in cell culture. The complete sequence of the E5-651 virus genome rescued from cDNA in Vero or CEF cells was determined by analysis of overlapping RT-PCR cDNA fragments, derived directly from virus RNA, and compared with the consensus sequence of its parental E5 virus as well as the nucleotide sequence of the viral insert in the pE5-651 plasmid from which infectious RNA transcripts were derived (Table I). The rescued E5-651 clone contained the E5 consensus sequence in the 12 positions at which the wild-type TP21 parent differed from its E5 derivative. Analysis of the plasmid DNA revealed eight differences in nucleotide sequence from the consensus sequence of E5, of which three produced an amino acid substitution in the envelope structural protein E ($Glu_{149}$→Gly and $Glu_{291}$→Gly) and nonstructural protein NS4B ($Ala_{183}$→Val).

The sequence of the first passage Vero cell grown clone E5-651 did not differ from the plasmid cDNA sequence, whereas after 12 passages in Vero cells fluctuation between (i) $Ser_{17}$ and Asn and (ii) $Gln_{383}$ and Lys was identified in NS2B and NS3, respectively. E5-651 rescued and passaged once in CEF cells differed from the plasmid DNA sequence at 2 nt positions in E; one of the changes resulted in fluctuation between C and U at nt position 1151 of E and fluctuation between $Gly_{149}$ and Arg at nt position 1415 of E. When CEF cell culture-derived virus was passaged an additional 11 times in CEF cells, only U (nt 1151) or A (nt 1415) was selected from the fluctuation mixture. In addition, 4 other substitutions were identified, two of which a produced a coding change (Table I). In contrast, only two positions 4254 (G/A) and 5744 (C/A) in genome sequence varied after 12 passages of E5-651 virus in Vero cells. Because the frequency of E5-651 genomic changes in CEF cells was greater than that observed in Vero cells, the Vero cell culture-derived E5-651 virus was selected on the basis of its apparent greater stability to be used for analysis of mouse neuroinvasiveness, Before evaluating virus virulence in mice, E5-651 virus was subjected to plaque-to-plaque purification to minimize the accumulation of spontaneous mutations, which might occur during virus amplification in Vero cells.

Plaquing efficiency and purification of E5 clone in cell culture. Plaque phenotype of the rescued E5-651 virus recovered from Vero cells and passaged once in these cells was examined using simian $LLCMK_2$ and Vero cells. The rescued Vero cell culture-derived E5-651 virus produced small clear transparent plaques 1.5 mm in diameter on $LLCMK_2$ cells 7 days post-infection (Table II). In contrast, this virus produced smaller (<0.1 mm) faint plaques in Vero cells. In comparison, parental E5 virus grown in Vero cells produced large plaques (5.0 to 5.2 mm) on both Vero and $LLCMK_2$ cells. Clone E5-651 rescued and grown in CEF cells exhibited the same plaque size and morphology in the two simian cell cultures as Vero cell-derived virus.

Individual 1.5 mm plaques of E5-651 were harvested from $LLCMK_2$ cells infected with Vero cell culture-derived virus and then subjected to three additional plaque-to-plaque passages in $LLCMK_2$ cells. Seed stock of the plaque-purified isolate of E5-651 virus was prepared following further amplification in Vero cells. Difference of plaque phenotype of the E5-651 virus in Vero and $LLCMK_2$ cells did not change following plaque-to-plaque selection in $LLCMK_2$ cells and amplification in Vero cell culture. In addition, the plaque-purified isolate did not differ in sequence from its rescued E5-651 virus.

Evaluation of cDNA-derived E5 virus in mice. Previously, wild-type strain TP21 was shown to be virulent for 3-week-old Swiss mice with an intraperitoneal $LD_{50}$ of $5\times10^3$ PFU (Pletnev, A. G., and Men, R. (1998). Attenuation of the Langat tick-borne flavivirus by chimerization with mosquito-borne flavivirus dengue type 4. Proc. Natl. Acad. Sci. USA 95, 1746–1751.). In contrast, the attenuated E5 strain derivative of TP21 exhibited neuroinvasiveness in adult mice only when the amount of virus inoculated was increased to $10^7$–$10^8$ PFU. In the earlier study SCID mice were shown to be at least $10^6$- to $10^8$-times more permissive than normal mice for detection of peripheral neurovirulence of Langat virus strains. For this reason, 3-week-old SCID mice in groups of 5 were inoculated IP with decimal dilutions of E5-651 or with 1 PFU of parental E5 strain whose $LD_{50}$ had previously been determined to be 0.06 PFU (Pletnev, A. G., and Men, R. (1998) Attenuation of the Langat tick-borne flavivirus by chimerization with mosquito-borne flavivirus dengue type 4. Proc. Natl. Acad. Sci. USA, 95, 1746–1751.). $10^5$ PFU of chimera TP21/DEN4(vac) was also evaluated IP in SCID mice as a negative, control because an earlier study indicated that it lacked any evidence for neuroinvasiveness (IP $LD_{50}$ of $>10^7$ PFU) (Pletnev, A. G., and Men, R. (1998) Attenuation of the Langat tick-borne flavivirus by chimerization with mosquito-borne flavivirus dengue type 4. Proc. Natl. Acad. Sci. USA, 95, 1746–1751.). Parental E5 virus caused 100% mortality within 9 to 13 days after IP inoculation of 1 PFU, whereas $10^5$ PFU of the chimeric virus failed to cause fatal disease over a period of 7 weeks. However, 2 of 5 mice died 28 or 33 days following IP inoculation of 100 PFU of E5-651. In a subsequent experiment, groups of five SCID mice were inoculated IP with decimal dilutions of clone E5-651, and its $LD_{50}$ was determined to be 20.4 PFU (21.0 PFU in repeat experiment). Thus, done E5-651 was $5.1\times10^3$ times less neuroinvasive than strain TP21 which had an estimated $LD_{50}$ for SCID mice of 0.004 PFU and $3.4\times10^2$ times less virulent than its immediate parental E5 virus which had an estimated $LD_{50}$ of 0.06 PFU for SCID mice (Pletnev, A. G., and Men, R. (1998). Attenuation of the Langat tick-borne flavivirus by chimerization with mosquito-borne flavivirus dengue type 4. Proc. Natl. Acad. Sci. USA 95, 1746–1751.).

Construction of 3'-NCR deletion mutants and virus recovery. In attempt to increase the level of attenuation of clone E5-651 for SCID mice, several strategic mutations were introduced in its cDNA genome. With regard to the development of an attenuated live flavivirus vaccine, any attenuating mutations introduced into the candidate vaccine virus should be genetically stable and not able to effect a significant reduction in immunogenicity and protective efficacy. Recent studies involving several flaviviruses suggest that 3'-NCR deletions meet these requirements (Men, R., Bray, M., Clark, D., Chanock, R. M., and Lai, C.-J. (1996). Dengue type 4 virus mutants containing deletions in the 3' noncoding region of the RNA genome: analysis of growth restriction in cell culture and altered viremia pattern and immunogenicity in rhesus monkeys. J. Virol. 70, 3930–3937.; Mandl, C. W., Holzmann, H., Meixner, T., Rauscher, S., Stadler, P. F., Allison, S. L., and Heinz, F. X. (1998). Spontaneous and engineered deletions in the 3' noncoding region of tick-borne encephalitis virus: construction of highly attenuated mutants of a flavivirus. J. Virol. 72, 2132–2140.). The 3'-NCR of the RNA genome of tick-borne flaviviruses varies from 393 to 800 nt in length, of which only the last approximately 340 nts (core element) are more conserved than the region between the stop codon of the open reading frame and the core element (Dobrikova, E. Yu., and Pletnev, A. G. (1995). A full-size DNA copy of the tick-borne encephalitis virus genome. Part I. Analysis of noncoding 5'- and 3'-regions. Bioorganic Chemistry 21, 528–534.; Mandl, C. W., Holzmann, H., Meixner, T., Rauscher, S., Stadler, P. F., Allison, S. L., and Heinz, F. X. (1998). Spontaneous and engineered deletions in the 3' noncoding region of tick-borne encephalitis virus: construction of highly attenuated mutants of a flavivirus. J. Virol. 72, 2132–2140.). A recent study of TBEV provided evidence that a 3'-NCR deletion could reduce virulence without loss of viability if the deletion extended from the stop codon of the viral polyprotein to the beginning of the core element (Mandl, C. W., Holzmann, H., Meixner, T., Rauscher, S., Stadler, P. F., Allison, S. L., and Heinz, F. X. (1998). Spontaneous and engineered deletions in the 3' noncoding region of tick-borne encephalitis virus: construction of highly attenuated mutants of a flavivirus. J. Virol. 72, 2132–2140.).

We introduced deletions that start at the fifth nucleotide following the TAA-stop codon of the long open reading frame and extend to targeted nucleotides indicated in FIG. I (B and C). All mutant constructs contained an additional 3 or 5 nucleotides that created an AflII restriction enzyme cleavage site at the site of deletion (FIG. IC). The final mutant plasmids pE5-3'-320, pE5-3'-374, pE5-3'-449 and pE5-3'-471 contained a deletion 320, 374, 449 or 471 nt in length, respectively.

Vero cells were transfected with full-length genomic RNA transcripts prepared from full-length cDNA of the 3'-NCR deletion mutants described above. Only E5-3'-320 mutant RNAs yielded viable virus. These results were consistent with those observed for TBEV 3'-NCR deletion mutants (Mandl, C. W., Holzmann, H., Meixner, T., Rauscher, S., Stadler, P. F., Allison, S. L., and Heinz, F. X. (1998). Spontaneous and engineered deletions in the 3' noncoding region of tick-borne encephalitis virus: construction of highly attenuated mutants of a flavivirus. J. Virol. 72, 2132–2140.). Extension of deletion into the core element of the 3' end TBEV or LGT genome abolishes virus viability. The longest deletion of TBEV compatible with viability retains the last 222 nts of the 3' end. The 3'-NCR of rescued E5-3'-320 virus retains the last 244 nts of its genome.

Characterization of the rescued 3'-NCR deletion mutant. The rescued E5-3'-320 differed from the E5-651 done with respect to plaque morphology in simian cells. The 3'-NCR deletion mutant failed to produce visible plaques on Vero cells, the cell substrate in which this virus was recovered (Table II). The mutant produced plaques on $LLCMK_2$ cells, but they were very small, less than 0.2 mm. Such individual plaques were harvested and then subjected to three plaque-to-plaque passages in the $LLCMK_2$ cell line. Finally, seed stock suspension of E5-3'-320 virus was prepared by additional amplification in Vero cells. The complete genome sequence of the E5-3'-320 mutant was determined and compared with sequence of E5-651 clone. The only difference detected was the 3'-NCR deletion of the E5-3'-320 mutant.

The replication efficacy of parental E5, recombinant E5-651 and its 3'-NCR deletion mutant was assayed using $LLCMK_2$ or Vero cells inoculated with a multiplicity of infection (MOI) of 0.01 (FIG. II). In Vero cells growth of E5-3'-320 was $10^4$ less than that of its E5-651 parent or E5 parent itself. The deletion mutant also grew less well in $LLCMK_2$ cells but it was restricted only 9 to 50-fold (FIG. II and Table II).

Neuroinvasiveness of 3'-NCR deletion mutant in SCID mice. Neuroinvasiveness of E5-651 and its E5-3'-320 deletion mutant was evaluated in SCID mice in groups of 5 inoculated IP with decimal dilutions of virus. The recombinant 3'-NCR deletion mutant was less virulent for SCID mice than its immediate E5-651 parent. The estimated IP $LD_{50}$ for E5-3'-320 was 479 PFU compared to 20.4 PFU for E5-651. Overall, the cloned E5-651 and E5-3'-320 viruses were 5,100 and 119,750 times less neuroinvasive, respectively, than their wild-type progenitor, LGT TP21 virus.

Characterization of virus recovered from the brain of moribund SCID mice inoculated IP with E5 or its recombinant derivatives. Death of mice inoculated IP with E5-651 or E5-3'-320 was delayed by a factor of 2 compared to that of mice inoculated with their biologically derived E5 parent (Pletnev, A. G., and Men, R. (1998). Attenuation of the Langat tick-borne flavivirus by chimerization with mosquito-borne flavivirus dengue type 4. Proc. Natl. Acad. Sci. USA 95, 1746–1751.). This delay is consistent with the increase in attenuation of the recombinant viruses as measured by IP $LD_{50}$ in SCID mice. In an attempt to explain the observed significant delay in onset of encephalitis we sequenced the full genome of the brain isolates and compared the sequence to that of the virus that was inoculated IP (Table III). The brain isolates differed from the virus used to initiate infection by at most 3 coding changes in E, NS1, NS2B, NS3, NS4B or NS5. Three of the brain isolates sustained 3 coding changes, while the remaining 2 viruses differed from inoculated virus at only one amino acid position. Two brain isolates from SCID mice inoculated IP with 4.9 $LD_{50}$ or 49 $LD_{50}$ of recombinant E5-651 shared two coding changes, one at nt 1571 [G→A ($Ala_{201}$→Thr) or G→G/A ($Ala_{201}$→Ala/Thr)] and the other at nt 5794 [G→U ($Glu_{399}$→Asp) or G→G/U ($Glu_{399}$→Glu/Asp)]. All of the other 7 coding changes were unique, i.e., not shared with other isolates.

In an initial attempt to clarify this situation, a mouse brain isolate of E5-651 that contained the unique amino acid substitution ($His_{130}$→Tyr) in E (Table III) was passaged once in Vero cells and then tested in 5 SCID mice by IP inoculation of 1 or 10 PFU. All inoculated mice died during the 14 day observation period. In addition, the mouse brain isolate of E5-3'-320 virus that contained the unique amino acid substitution ($Gly_{149}$→Glu) in E (Table III) and that was also passaged once in Vero cells was lethal for 100 or 80% of SCID mice inoculated IP with 1,000 or 100 PFU, respectively. These findings suggest that the observed spontaneous mutations in neuroinvasive isolates of the recombinant E5-651 and E5-3'-320 are responsible for the increased neroinvasiveness of these mutants in immunodeficient mice.

Immunogenicity and protective efficacy of parental E5 and its recombinant E5-651 or E5-3'-320 virus. Three-week-old outbred Swiss female mice (7–9 g) were inoculated IP with decimal dilutions of parental E5 or its cDNA-derived E5-651 or E5-3'-320 virus (Table IV). Twenty-two days after inoculation, immunized as well as nonimmunized (control) mice were bled to measure the titer of serum neutralizing antibodies against LGT TP21. All immunized mice seroconverted. Mice immunized IP with 10 PFU of parental virus or either of its recombinants developed a moderate to high titer of neutralizing antibodies against LGT TP21. However, immunization with 10 or 100 fold more virus increased the titer of TP21 neutralizing antibodies attained. There was no significant difference in the highest serum antibody titer induced by parental E5 or either of its recombinant derivatives in Swiss mice.

On day 23 post-immunization, mice were challenged IP with 2,000 IP $LD_{50}$ of the wild-type LGT TP21 strain. Mice immunized IP with 10 PFU of E5, or E5-651, or E5-3'-320 were completely protected against lethal TP21 challenge, whereas none of the control mice survived challenge. It is noteworthy that the more attenuated mutant (E5-3'-320) which exhibited restricted growth in cell culture and a significant reduction in neuroinvasiveness for SCID mice was able to induce complete protective immunity in immunocompetent mice at such a low immunization dose. These data provide a basis for proposing that the E5-3' deletion mutant be considered a candidate vaccine strain that is envisioned as serving as a stand-alone vaccine. Alternatively, this mutant could provide a foundation for further alteration to yield a live virus vaccine for use in preventing disease caused by antigenically-related tick-borne flaviviruses.

EXAMPLES

Infectious cDNA Clones of Langat Tick-borne Flavivirus that Differ from their Parent in Peripheral Neurovirulence Three different methods were employed to construct full-length cDNA clones of LGT TP21. These methods used the following molecular biology techniques.

Cells and virus preparations. Simian Vero, $LLCMK_2$, and BHK cells were purchased from the American Type Culture Collection. Cells were grown in MEM with 1% glutamine, 10% fetal bovine serum, 50 μg/ml gentamicin, 0.25 μg/ml fungizone at 37° C. and 5% $CO_2$. Virus stocks of the Langat (LGT) wild type strain TP21, its further attenuated E5 mutant and their TP21/DEN4 and E5/DEN4 chimeras were prepared in Vero cells as described previously (Pletnev, A. G., and Men, R. (1998) Attenuation of the Langat tick-borne flavivirus by chimerization with mosquito-borne flavivirus dengue type 4. Proc. Natl. Acad. Sci. USA, 95, 1746–1751.). The LGT wild-type strain TP21 strain is available from the Rockefeller Foundation Collection. (Gordon Smith, C. E. (1956) A virus resembling Russian spring-summer encephalitis virus from an Ixodid in Malaya. Nature (London) 178, 581–582.). The LGT E5 is available from U.S. Army Medical Research Institute of Infectious Diseases. (Thind, I. S., and Price, W. H. (1966a) A chick embryo attenuated strain (TP21 E5) of Langat virus. I. Virulence of the virus for mice and monkeys. Am. J. Epidemiol., 84, 193–213.).

Vero cells in 150-$cm^2$ tissue culture flasks were infected with TP21 or E5 virus at a multiplicity of infection of 0.01. After adsorption at 37° C. for 1 hr, virus inoculum was removed and fresh medium was added. The contents of a single flask was harvested on day 1, 2 or 5 following virus infection, and virus titer was determined by plaque assay on Vero cells which were stained with neutral red to visualize plaques 7 days post-infection. Titer of these three virus stocks was $3.8\times10^3$, $2.2\times10^6$ and $2.4\times10^9$ PFU/ml for TP21 and $1.2\times10^4$, $4\times10^6$ and $1.2\times10^9$ PFU/ml for E5.

Reverse transcription. Virus in supernatant of cell culture medium was precipitated by 8% polyethylene glycol 8000 (US Biochemical Corp., Cleveland, Ohio) and 0.4M NaCl overnight at 4° C. and collected by centrifugation. Total RNA was extracted from virions using TRI Reagent (Molecular Research Center, Inc., Cincinnati, Ohio). Reverse transcription (RT) was performed with SuperScript II Preamplification system (Life Technologies, Rockville, Md.) and (i) an oligonucleotide (oligo) (1445) 5'-GCCTGC GGAGGGTACCGATATCAGCGGGTGTTTTTCCG AGACACG (SEQ ID NO 3) that is complementary to the LGT sequence at its 3' terminus, i.e., nucleotides (nts) 10,921–10,943, and contains the EcoRV and KpnI site immediately following the LGT 3' end sequence or (ii) an oligo (1087) 5'-CTATGGCCAGGTGGAAAGCCGC (SEQ ID NO 4) that is complementary to the LGT sequence at nts 7256–7277. The latter oligo was used to facilitate transcription of the 5' end of the genome. Prior to reverse transcription, 5–10 μg of RNA and 100 ng of primer were incubated at 70° C. for 5 min and then chilled on ice. RT reaction mixtures contained this heat-denatured RNA plus ingredients of SuperScript II kit (Life Technologies, Rockville, Md.) and 200 U reverse transcriptase in a final volume 100 μl. The reaction mixtures were incubated at 42° C. for 2 hrs and then frozen and used as a template to generate double-stranded DNA by polymerase chain reaction (PCR) for construction and cloning of cDNA TP21 in *E. coli* or for sequence analysis of RT-PCR derived viral genome.

PCR. The standard PCR mixture used to produce double-stranded cDNA contained 0.5 μM each of primer pairs, 200 ng plasmid DNA or 5–10 μl of RT product as a template, 400 μM of dNTPs, 1×Buffer and 5 U Takara LA Taq DNA polymerase (Takara LA PCR kit, PanVera Co., Madison, Wis.) in a total reaction volume of 100 μl. The reaction mixture was preheated to 94° C. for 2 min and then subjected to 30 cycles, each cycle being 98° C. for 20 sec and 68° C. for 15 min.

Sequence analysis of viral genome. The complete sequence of (i) the TP21 genome, (ii) the genome of its more attenuated derivative strain E5 and (iii) TP21 virus recovered from cDNA was determined by sequence analysis of 4 overlapping RT-PCR cDNA fragments which were directly derived from virus RNA. The oligo 1445 or 1087 was used as a primer to obtain the first-strand cDNA by reverse transcription as described above. PCR was performed to amplify the four overlapping genome fragments: A (nt 1 to 4192), B (nt 3491 to 7277), C (nt 6131 to 9669) and D (nt 8857 to 10,943) using appropriate primers and Takara LA PCR kit. Primers for PCR and sequence analysis were designed using previously published LGT TP21 strain sequence (GenBank accession no. M86650 and M73835) (Mandl, C. W., Iacono-Connors, L., Wallner, G., Holzmann, H., Kunz, C., and Heinz, F. X. (1991) Sequence of the genes encoding the structural proteins of the low-virulence tick-borne flaviviruses Langat TP21 and Yelantsev. Virology 185, 891–895.; Iacono-Connors, L. C., and Schmaljohn, C. S. (1992) Cloning and sequence analysis of the genes encoding the nonstructural proteins of Langat virus and comparative analysis with other flaviviruses. Virology 188, 875–880.; Pletnev, A. G., and Men, R. (1998) Attenuation of the Langat tick-borne flavivirus by chimerization with mosquito-borne flavivirus dengue type 4. Proc. Natl. Acad. Sci. USA, 95, 1746–1751.). PCR products were purified in an agarose gel and isolated using a Qiagen Gel Extraction Kit (Valencia, Calif.). Sequence of RT-PCR fragments was determined using BigDye Terminator Cycle Sequencing Ready Reaction (PE Applied Biosystems/ABI Prism, Foster City, Calif.) and a Model 310 Genetic Analyzer.

To determine 3'- and 5'-end sequence of viral genome, RNA from rescued virus or from parental TP21 or E5 virus was treated with tobacco acid pyrophosphatase (Epicentre Technol. Co., Madison, Wis.) to cleave off the cap structure. And then the 5' and 3' termini of viral RNA were joined using T4 RNA ligase (New England Biolabs, Beverly, Mass.). Oligo 979 (complementary to LGT sequence at 1149–1167 nt) was used to generate first strand cDNA by RT. A double-stranded cDNA fragment containing the 5'- and 3'-end junction of genome was amplified by PCR using the primer pair oligo 916, positive-sense primer containing nts 10,349–10,382 of the LGT sequence and oligo 907, negative-sense primer complementary to 955–983 nts. The final PCR product, 1578 nt in length, was then sequenced.

EXAMPLE 1

Method 1: Subcloned Fragments of TP21 Genome from High Titered Virus Preparation This method employed four overlapping cDNA fragments (FIG. 1, part A) previously cloned in *E. coli* for use in determining the complete nucleotide sequence of LGT TP21 genome (Pletnev, A. G., and Men, R. (1998) Attenuation of the Langat tick-borne flavivirus by chimerization with mosquito-borne flavivirus dengue type 4. Proc. Natl. Acad. Sci. USA, 95, 1746–1751.). These plasmid clones, namely p5 (LGT nts 1 to 983), p44 (nts 930 to 4828), p66 (nts 4539 to 6571) and p76 (nts 6525 to 10,943) were derived from a LGT cDNA library prepared from a high titered virus suspension, $1.8\times10^9$ PFU/ml. The DNA fragment p5 was amplified by PCR using the sense primer (oligo 1444) 5'-GAAGGTGGTCTTTGCGGCCGCATCATACACATAC GATTTAGGTGACACTATAGAGATTTTCTTGCGC GTGCATGC (SEQ ID NO 1), which included the NotI site and the SP6 promoter immediately upstream of the 1–22 nts of the 5' end of genome, while the negative-sense primer (oligo 907) 5-GGGTGCATCTCGACGCGTAGGCCGG TACC (SEQ ID NO 2) was complementary to LGT nts 955–983 and contained KpnI cleavage site. The PCR product was digested by a NotI and a KpnI and ligated to similarly digested p44. The resulting large subgenomic clone (p49), representing the TP21 genome from its 5' terminus to nt 4828 and containing a unique ApaI cleavage site at position 4801, was sequenced in its entirety. The EcoRV and KpnI cleavage sites were incorporated into the TP21 cDNA immediately downstream of the 3'end of genome during of construction of p76 plasmid. LGT cDNA fragments from p66 and p76 were joined to form a larger cDNA clone by ligation using a unique NsiI restriction site (position 6551 of LGT genome) and a PvuI site of the vector. The resulting clone p77 containing the 3'-half of the genome (from nt 4539 to the 3' end of genome plus EcoRV and KpnI site) was sequenced and then used for assembly of the final plasmid construct. Construction of full-length TP21 cDNA was completed by ligation of plasmid p77, which had been digested with NotI and ApaI, and the NotI-ApaI-fragment of p49. Ten stable individual full-length cDNA clones were identified after transfection of *E. coli* strain BD1528 with ligation mixture. Screening of plasmids indicated that these stable clones exhibited the expected restriction pattern when tested with EcoRI, PstI and SalI.

In addition, a separate set of full-length cDNA clones was prepared using the plasmid cDNA designated p76 (nts 6525 to 10,943) ligated to a long PCR cDNA fragment that included the 5' terminal nucleotide (nts 1 to 6571) and overlapped p76 (FIG. 1, part A). The longest cDNA clones produced in this manner by ligation were cloned in *E. coli*. Two stable full-length cDNA clones were recovered.

Prior to RNA transcription, each of the twelve pFL-TP21 plasmids selected for apparent genome length were digested with EcoRV and precipitated with ethanol after phenol-chloroform extraction of proteins.

EXAMPLE 2

Method 2: Long RT-PCR cDNA of Viral Genome

This method employed long RT-PCR in a separate attempt to derive viral genome length cDNAs. Two different virus suspensions were used as the source for viral cDNAs; one suspension harvested on day 2 had a low titer ($3.8\times10^3$ PFU/ml) while the other suspension harvested on day 5 had a high titer ($2.4\times10^9$ PFU/ml). The PCR mixture contained primers (oligo 1444 and 1445), 10 $\mu$l of RT product as a template and Takara LA PCR (PanVera Co., Madison, Wis.) kit ingredients, including 5 U DNA polymerase. The PCR products, approximately 11 kb in length, were separated from lower molecular weight DNA by electrophoresis (FIG. 2) in an agarose gel and isolated from gel using a Qiagen gel extraction kit (Venlo, The Netherlands). Prior to use as a template for RNA transcription, the PCR product was digested by EcoRV and purified by phenol-chloroform extraction. RNA transcripts (approximately 1 $\mu$g) of these cDNAs were then transfected into Vero cell culture, which was then monitored for evidence of infection by immunofluorescence.

EXAMPLE 3

Method 3: Construction of Full-length cDNA Clones from Two Overlapping PCR Fragments Derived from Low Titered Virus This method employed two overlapping cDNA fragments that included the entire sequence of TP21 (FIG. 1, part C). These fragments were derived from a virus suspension of low titer ($3.8\times10^3$ PFU/ml). For the 5' half of LGT genome, a PCR product was generated by using the sense primer (oligo 1444) which included the NotI site, the SP6 promoter and 1–22 nts of LGT sequence and the negative-sense primer (oligo 1023) 5'-CCCAGGGTTGCAAGCCCCAGG (SEQ ID NO 5) that was complementary to LGT nts 6637–6657. PCR was employed to derive the 3' half of LGT genome using the positive-sense primer (oligo 971) 5'-TTGCACCTGACTGAACTGGAG (SEQ ID NO 6) that was complementary to LGT nts 4451–4471 and oligo 1445 as a negative-sense primer.

Initially, the full-length cDNA genome was constructed by joining these two PCR fragments using NotI and KpnI cleavage sites of p2A(XhoI) vector (Bray, M., and Lai, C.-J. (1991) Construction of intertypic chimeric viruses by substitution of structural protein genes. Proc. Natl. Acad. Sci. USA, 88, 10342–10346.) and a unique ApaI site which is present in both RT-PCR fragments (FIG. 1). However, this strategy to prepare full-length cDNA failed because the clones were unstable in *E. coli*. Subsequently the two long fragments were assembled into a stable full-length cDNA in a two step cloning procedure.

During the first step, the PCR product representing the 3' half of genome (nts 4451 to 10,943) was cloned in *E. coli* using plasmid p51 as a vector. Plasmid p51 was created by inserting a small BamHI-PstI-fragment (nts 4539 to 5349) of TP21 cDNA, which was obtained by PCR using appropriate primers, into a unique BglII and PstI site of the p5'-2(NotI, XhoI, ΔHindIII) vector (Cahour, A., Pletnev, A., Vazeille-Falcoz, M., Rosen, L., and Lai, C.-J. (1995) Growth-restricted dengue virus containing deletions in the 5' noncoding region of the RNA genome. Virology 207, 68–76.). In addition, plasmid p51 contained a NotI cleavage site, SP6 promoter and the first 88 nts of Dengue type 4 virus genome. It was used as a vector because it possessed a unique ApaI cleavage site. The PCR product (LGT nts 4451–10,943) was digested with ApaI and KpnI and then cloned into the ApaI-BamHI-digested region of the p51 vector together with a KpnI-BamHI-fragment derived from p5'-2A(XhoI). After transformation of bacteria with ligation mixture, a clone (p624-3) that contained LGT nts from 4539 to the 3' end of genome was selected based on its restriction pattern.

During the second step, the PCR product representing the 5' half of genome (nts 1 to 6657) was digested with NotI and ApaI and then cloned into p624-3, generating full-length cDNA clones of pTP21. Twenty-eight individual full-length LGT TP21 cDNA clones were stable in the plasmid vector when propagated in *E. coli* strain BD1528. However, some polymorphism was observed among the stable full-length LGT cDNAs with respect to restriction enzyme digestion pattern. The viral sequences of four plasmids that served as template for infectious RNA transcripts were verified. These four plasmids were designated as pTP21-636, pTP21-649, pTP21-656 and pTP21-689 and the corresponding number was used to designate rescued virus.

EXAMPLE 4

RNA Transcription, Transfection, and Recovery of Virus

Each of the 28 stable pTP21 plasmids containing full-length TP21 cDNA produced by method 3 (FIG. 1) was linearized with EcoRV, extracted with phenol-chloroform, and ethanol precipitated. For in vitro RNA synthesis, the transcription reaction mixture contained 5 $\mu$g of linearized DNA; 1 mM cap analog $m^7G(5')ppp(5')G$ (New England BioLabs, Beverly, Mass.); 0.5 mM each ATP, CTP, and UTP; 10 mM DTT; 1×polymerase buffer; 100 U of RNase inhibitor; 50 U of SP6 RNA polymerase (Promega, Madison, Wis.) in a volume of 100 $\mu$l. The reaction mixture was incubated at 37° C. for 1 hr, and the DNA template was then digested with 3 U of RQ1 DNase (Promega, Madison, Wis.) for 10 min at 37° C. The typical yield of RNA was approximately 10 $\mu$g as determined by agarose gel electrophoresis analysis.

RNA transcripts of the full length LGT constructs were used to transfect subconfluent monolayers of simian Vero or $LLCMK_2$ cells or hamster BHK cells in the presence of transfection reagent LipofectAmine (Gibco BRL, Gaithersburg, Md.) or DOTAP (Roche Molecular Biochemicals, Indianapolis, Ind.) as described previously (Pletnev, A. G., Bray, M., and Lai, C.-J. (1993) Chimeric tick-borne encephalitis and dengue type 4 viruses: effects of mutations on neurovirulence in mice. J. Virol., 67, 4956–4963.). On day 5 and again on days 10, 15 and 20, cells were split and passaged. Cells cultured in slide chambers were examined on each of these occasions by IFA for the presence of LGT proteins using a LGT-specific mouse antiserum or LGT-specific HMAF. When 80–100% of cells were positive as indicated by IFA, the contents of infected T-75 flasks were collected, frozen and later used for characterization of cDNA-derived LGT virus. These recombinant LGT viruses were amplified twice in simian Vero cells, after which viral RNA was isolated and reverse transcribed for cDNA amplification and sequence analysis. The procedures used for plaque assay, analysis of replication in cell culture and radioimmunoprecipitation of virus-specific proteins were described earlier (Pletnev, A. G., Bray, M., Huggins, J., and Lai, C.-J. (1992) Construction and characterization of tick-borne encephalitis/dengue type 4 viruses. Proc. Natl. Acad. Sci. USA, 89, 10532–10536.; Pletnev, A. G., Bray, M., and Lai, C.-J. (1993) Chimeric tick-borne encephalitis and dengue type 4 viruses: effects of mutations on neurovirulence in mice. J. Virol., 67, 4956–4963.).

EXAMPLE 5

Evaluation of cDNA-derived Viruses in Mice

Peripheral neurovirulence ("neuroinvasiveness") of parental and cloned TP21 viruses was evaluated in 3-week-old outbred Swiss mice that were inoculated by the IP route in groups of 5 with $10^4$ or $10^6$ PFU of virus and observed for 28 days for fatal or nonfatal encephalitis. A considerably more sensitive assay for neuroinvasiveness of LGT virus that used immunodeficient (SCID) mice was also employed for analysis of this important virulence phenotype (Pletnev, A. G., and Men, R. (1998) Attenuation of the Langat tick-borne flavivirus by chimerization with mosquito-borne flavivirus dengue type 4. Proc. Natl. Acad. Sci. USA, 95, 1746–1751.). In this assay, female 3-week-old C.B.-17 Icr/scid/scid mice (Taconic Farm, Germantown, N.Y.) in groups of five were inoculated IP with (i) $10^2$ PFU parental TP21, or E5, or TP21 derived from cDNA or (ii) with $10^5$ PFU of chimeric TP21/DEN4 or E5/DEN4 virus or (iii) decimal dilutions of rescued recombinant virus ranging from 1 to $10^2$ PFU. These mice were observed for mortality for 7 weeks.

Infectious cDNA Clone of Attenuated Langat Tick-borne Flavivirus (Strain E5) and a 3' Deletion Mutant Constructed from it Exhibit Decreased Neuroinvasiveness in Immunodeficient Mice Cells and virus preparations. Certified Vero cells (W.H.O. Seed, 143 passage) were obtained from Novavax Inc. (Rockville, Md.). Primary chicken embryonic fibroblast (CEF) cells were kindly provided by Dr. Linda Wyatt (NIAID, NIH, Bethesda, Md.). Simian $LLCMK_2$ cells were purchased from the American Type Culture Collection. Cells were grown in MEM with 1% glutamine, 10% fetal bovine serum, 50 $\mu$g/ml gentamicin, 0.25 $\mu$g/ml fungizone at 37° C. and 5% $CO_2$. Virus stocks of the LGT wild-type strain TP21 and its further attenuated E5 mutants were prepared in Vero cells as described earlier.

Reverse transcription and PCR. These procedures were performed as described earlier.

Sequence analysis of viral genome. The complete sequence of the genome of (i) E5, (ii) E5 recovered from cDNA and (iii) E5 or its derivatives isolated from the brain of moribund mice on day 14 or 28 post-infection was determined by sequence analysis of 4 overlapping RT-PCR cDNA fragments which were derived directly from virus RNA. The oligo 1445 was used as a primer to obtain the first-strand cDNA by reverse transcription as described above. PCR was performed to amplify the four overlapping genome fragments: A (nt 1 to 4192), B (nt 3491 to 7277), C (nt 6131 to 9669) and D (nt 8857 to 10,943) using appropriate primers and Takara LA PCR kit. Primers for PCR and sequence analysis were designed using previously published LGT sequence (GenBank accession no. AF253419 and AF253420). PCR products were purified in an agarose gel and isolated using a Qiagen gel extraction kit. Sequence of RT-PCR fragments was determined using BigDye Terminator Cycle Sequencing Ready Reaction (PE Applied Biosystems/ABI Prism, Foster City, Calif.) and a model 310 Genetic Analyzer.

EXAMPLE 6

Method I: Construction of Full-length cDNA of LGT E5

(FIG. IA). A long RT-PCR cDNA fragment of E5 genome and plasmid pTP21-636, which contains full-length infectious cDNA of LGT TP21 were used for this purpose. Plasmid pTP21-636 was digested with SfiI and AgeI, whose sites were unique in this vector. Almost full-length cDNA (approximately 10.5 kb) of E5 genome was produced (FIG. IA) by high-fidelity PCR using a positive-sense primer 1484 that contained the first 23 nts of LGT sequence, and a negative-sense primer 1107 that was complementary to the LGT nts 10,439–10,460 of the 3' terminus. This RT-PCR fragment was derived from a E5 virus suspension of low titer ($1.2\times10^4$ PFU/ml). The PCR product (LGT E5 nts 1–10,460) was digested with SfiI and AgeI and then cloned into the SfiI(133)-AgeI(9737)-part of the pTP21-636 vector (nucleotide numbers indicate the first base of the recognition site sequence and correspond to the full-length sequence of LGT genome), which contained a NotI cleavage site, SP6 promoter and the first 133 nts and nts 9737–10,943 of LGT TP21 genome that are completely conserved in E5. There were also EcoRV and KpnI cleavage sites, which were incorporated into the LGT cDNA immediately downstream of the 3' end of genome (FIG. I). The resulting pE5 clones that contained LGT E5 were identified by restriction enzyme analysis and sequence analysis of genomic regions where TP21 and E5 genomes differed. Six individual full-length E5 cDNA clones (plasmids pE5) were stable in the plasmid vector when propagated in *E. coli*. The complete viral sequence of one of these six plasmids was determined; this plasmid was designated as pE5-651 and the corresponding number was used to designate rescued virus.

EXAMPLE 7

Method II: Introduction of Deletions into Full-length LGT E5 cDNA (FIGS. IB and IC). To introduce deletions into the 3' NCR of the E5 genome, PCR-generated subfragments between the AgeI site (nt 9737) and the KpnI site at the 3' end were cloned in the p624-3 vector, which contains these unique cleavage sites. The unique AflII site (nt 10,379) was introduced downstream of the TAA-stop codon in the 3' NCR of E5-651 genome (FIGS. IB and IC). The first PCR-amplified fragment was produced using pE5-651 plasmid as a template and the positive-sense primer (oligo 1013) that contains 9603–9623 nts of LGT genome and the negative-sense primer (oligo 1638) 5'-TTGGACTCCTTGCTTAAGGCT<u>TTA</u>AAATATTGAGCTCTC (SEQ ID NO 7) (the AflII site sequence is in bold, and the stop anticodon is underlined). This PCR fragment was digested with AgeI and AflII. Four deletions downstream of AflII site, 320, 374, 449, or 471 nts in length were introduced by PCR using the negative-sense primer (oligo 1445), which contains the complementary sequence of the last 23 nts at the LGT 3' terminus and the EcoRV and KpnI site and the positive-sense primer (oligo 1640, 1641, 1642 or 1643), which contains the targeted deletion sequence and the flanking AflII site. The sequence of these mutagenic primers were as follows: for the 320 nt deletion between 10,379–10,700 nts, oligo 1640, 5'-ACTGGGCGTTATCTTAAGGCCCCAGGGGGGAAACCCCTG (SEQ ID NO 8); for the 374 nt deletion between 10,379–10,754 nts, oligo 1641, 5'-GGATATTTCCTCCTTAAGATACCAAATGTCCCCTCGTCA (SEQ ID NO 9); for the 449 nt deletion between 10,379–10,829 nts, oligo 1642, 5'-CCCCTCGTCAGACTTAAGGGGGGGCGGTTCTTGTTCTCC (SEQ ID NO 10); for the 471 nt deletion between 10,379–10,851 nts, oligo 1643, 5'-ACGGACGTGCGCCTTAAGAAACTTTGTGAGACCCCTTGC (SEQ ID NO 11). PCR fragments were digested with AflII and KpnI, and then cloned into the AgeI-KpnI-digested region of the p624-3 vector together with an AgeI-AflII-fragment derived from first PCR as described above. After transformation of bacteria with ligation mixtures, the clones (p624-3'-320, p624-3'-374, p624-3'-449 and p624-3'-471) that contained the targeted deletions in the 3' NCR of genome were identified by sequence analysis. Construction of full-length E5 cDNA clones with deletions in 3' NCR of genome was completed by ligation of plasmid p624-3'-320, p624-3'-374, p624-3'-449, or p624-3'-471, which had been digested with NotI and AgeI, and the NotI-AgeI-fragment of pE5-651. The stable individual full-length E5 cDNA clones (pE5-3'-320, pE5-3'-374, pE5-3'-449 and pE5-3'-471), which contained deletion of 320, 374, 449 or 471 nts in length at 3' NCR of genome, were identified by sequence analysis.

EXAMPLE 8

RNA Transcription, Transfection, and Recovery of Virus

Each of the stable pE5 plasmids containing full-length LGT cDNA (FIG. I) was linearized with EcoRV, extracted with phenol-chloroform, and ethanol precipitated. For in vitro RNA synthesis, the transcription reaction mixture contained 5 μg of linearized DNA; 1 mM cap analog $m^7G(5')ppp(5')G$ (New England BioLabs, Beverly, Mass.); 0.5 mM each ATP, CTP, and UTP; 10 mM DTT; 1×polymerase buffer; 100 U of RNase inhibitor; 50 U of SP6 RNA polymerase (Promega, Madison, Wis.) in a volume of 100 μl. The reaction mixture was incubated at 37° C. for 1 hr, and the DNA template was then digested with 3 U of RQ1 DNase (Promega, Madison, Wis.) for 10 min at 37° C. The typical yield of RNA was approximately 10 μg as determined by agarose gel electrophoresis analysis.

RNA transcripts of the full-length LGT constructs were used to transfect subconfluent monolayers of CEF cells or simian Vero cells in the presence of transfection reagent LipofectAmine (Gibco BRL, Gaithersburg, Md.). On day 5 and again on days 10, 15 and 20, cells were split and passaged. Cells cultured in slide chambers were examined on each of these occasions by IFA for the presence of LGT proteins using a LGT-specific mouse antiserum or LGT-specific HMAF. When 80–100% of cells were positive by IFA, the contents of infected T-75 flasks were collected, frozen and later used for characterization of cDNA-derived LGT virus. These recombinant LGT viruses were amplified only once in simian Vero or CEF cells, after which viral RNA was isolated and reverse transcribed for cDNA amplification and sequence analysis. In a similar manner, the sequence of the Vero cell-derived or CEF cell-derived clone E5-651 was determined after an additional 11 passages in the corresponding cell line or after plaque-to-plaque purification on $LLCMK_2$ cells and one round of amplification on Vero cells.

The procedures used for plaque assay and analysis of replication in cell culture were described earlier (Pletnev, A. G., Bray, M., Huggins, J., and Lai, C.-J. (1992) Construction and characterization of tick-borne encephalitis/dengue type 4 viruses. Proc. Natl. Acad. Sci. USA, 89, 10532–10536.; Pletnev, A. G., Bray, M., and Lai, C.-J. (1993) Chimeric tick-borne encephalitis and dengue type 4 viruses: effects of mutations on neurovirulence in mice. J. Virol., 67, 4956–4963.). Also, the immunostaining focus-forming assay (Ishimine, T., Tadano, M., Fukunada, T., and Okuno, Y. (1987). An improved micromethod for infectivity assays and neutralization test of dengue viruses. Biken J. 30, 39–44.) was used in parallel with the plaque assay for determination of virus titer, because the recombinant viruses did not produce distinct plaques in Vero cells. Serial 10-fold dilution of virus suspension in MEM containing 2% heat inactivated fetal bovine serum (FBS) were inoculated (0.2 ml) into duplicate wells of 6-well or 24-well tissue culture plates containing monolayer of Vero or $LLCMK_2$ cells. After 1 hr of adsorption at 37° C., inoculum was removed and cells in 6-well plates were overlaid with agar and stained to revealed plaques with neutral red 7 days later. Cells in 24 well plates were overlaid with MEM containing 2% FBS, 50 $\mu$g/ml gentamicin, 0.25 $\mu$g/ml fungizone, and 1% tragacanth gum (Sigma Chemical Co., St. Louis, Mo.) and incubated for 4 days at 37° C. and 5% $CO_2$. Medium was removed, and the cell monolayers fixed for 30 min with methyl alcohol and rinsed twice with PBS. Cells in the wells were treated sequentially with 1:1000 diluted LGT-specific mouse antibodies and peroxidase labeled polymer conjugated to anti-mouse immunoglobulins (Dako Co., Carpinteria, Calif.) diluted 1:10 in PBS. Antibody-bound foci of infectious cells were developed using 0.01% $H_2O_2$ and 0.04% 3,3'-diaminobenzidine (Sigma Chemical Co., St. Louis, Mo.) in PBS and counted, and virus titer was expressed as a focus-forming unit per milliliter (FFU/ml).

EXAMPLE 9

Evaluation of cDNA-derived Viruses in Mice

In a previous study it was observed that immunodeficient (SCID) mice were $10^7$ to $10^8$ times more sensitive for detection of neuroinvasiveness than outbred Swiss mice (Pletnev, A. G., and Men, R. (1998). Attenuation of the Langat tick-borne flavivirus by chimerization with mosquito-borne flavivirus dengue type 4. Proc. Natl. Acad. Sci. USA 95, 1746–1751.). For this reason SCID mice were used for assay of neuroinvasiveness of LGT cDNA-derived virus E5 and its 3'-NCR deletion mutant. In this assay, female 3-week-old C.B.-17 Icr/scid/scid mice (Taconic Farms, Germantown, N.Y.) in groups of five were inoculated IP with decimal dilutions of cDNA-derived E5 (clone 651) and its 3'-NCR deletion mutant. These mice were observed for mortality for 7 weeks.

Blood, liver and brain of moribund mice which exhibited signs of advanced encephalitis, were harvested and a 10% tissue suspension was prepared in MEM, frozen and later used for virus isolation and sequence analysis. Titer of virus in these tissue suspensions was determined by plaque assay or focus-forming assay using monolayers of Vero or $LLCMK_2$ cells. 100 $\mu$l of the 10% tissue suspension was used for isolation of RNA, reverse transcription, cDNA amplification by PCR and for sequence analysis of recovered virus as described above. Also, the mouse brain isolate of E5-651 or E5-3'-320 virus was amplified in Vero cells and evaluated in the 3-week-old SCID mice in groups of 5 that were inoculated IP with decimal dilutions of virus.

Immunogenicity of parental E5 and recombinant E5-651 or E5-3'-320 viruses was evaluated in 3-week-old female Swiss mice that were inoculated IP with 10, $10^2$, $10^3$, or $10^4$ PFU. On day 22 post-inoculation, mice were bled to evaluate antibody response, challenged IP the next day with 2,000 IP $LD_{50}$ of TP21 virus, and observed for an additional 4 weeks.

For determination of LGT virus-neutralizing antibody titers, 10-fold diluted serum was heat inactivated for 30 min at 56° C. Serial two-fold dilutions of serum (starting at a serum dilution of 1:10) were mixed with equal volume of TP21 virus suspension containing approximately 100 FFU. The mixture was incubated for 30 min at 37° C., and 0.1 ml was added to duplicate wells of $LLCMK_2$ cells in a 24-well plate. After 1 hr of adsorption at 37° C., inoculum was removed and cells were overlaid with MEM containing 2% FBS, 50 $\mu$g/ml gentamicin, 0.25 $\mu$g/ml fungizone, and 1% tragacanth gum and titrated for infectious virus using the focus-forming assay as described above. Antibody titer was the highest dilution of antibody that reduced focus formation 50% compared to serum collected from non-immunized mouse.

EXAMPLE 10

Inducing an Immune Response from a Subject Administered an Amount of a Langat Virus It has been established that subhuman primates, but not other animals, are readily infected with flavivirus by the peripheral route (Simmons, et al., Phipp. J. Sci. 44:1–247, 1931 and Rosen, Am. J. Trop. Med. Hyg. 7:406–410 1958). Infection of monkeys represents the closest experimental system to flavivirus infection of humans. The response of rhesus monkeys to flavivirus infection is similar to that of humans in that there is a four to six day viremia, although lower primates do not develop clinical flavivirus symptoms. The objectives of flavivirus studies in monkeys are: (1) to evaluate the immunogenicity of various candidate vaccines; (2) to evaluate the infectivity and virulence (attenuation phenotype) of candidate live flavivirus vaccines as measured by the duration of viremia in days and the peak virus titer in PFU/ml; and (3) to evaluate the protective efficacy of the above-mentioned vaccines against challenge by flavivirus.

(1) Inoculation: Each rhesus monkey is inoculated with a total of $2\times10^5$ to $2\times10^7$ PFU of virus diluted in Eagle's minimal essential medium/0.25% human serum albumin. Normally, two subcutaneous doses are given to anesthetized animals.

(2) Blood collection: Following inoculation of virus, blood samples of 3.0 ml are taken daily for two weeks and 5.0 ml at 3 weeks, 4 weeks, 6 weeks, and 8 weeks.

(3) Challenge flavivirus: Where virus challenge is deemed appropriate to evaluate the protective efficacy, monkeys are inoculated with nonattenuated virus at $10^2$ to $10^5$ PFU/dose in a 0.5 ml volume subcutaneously in the upper arm area.

(4) Laboratory assays: Serum samples are used to determine: (a) the viremic duration by direct viral plaquing assay: (b) the titer of flavivirus specific antibodies by radio-immunoprecipitation and ELISA; and (c) the titer of neutralization antibodies by plaque reduction neutralization test, all tests well known to those skilled in the art of vaccine development.

While the present invention has been described in some detail for purposes of clarity and understanding, one skilled in the art will appreciate that various changes in form and detail can be made without departing from the true scope of the invention. All figures, tables, and listings, as well as patents, applications, and publications, referred to above, are hereby expressly incorporated by reference in their entireties.

TABLE 1

Differences between the genomic sequence of LGT strains TP21 and E5 as determined by sequence analysis of fragments of virus genome initially cloned in *E.coli* or tested directly after derivation by RT-PCR.

| Region | NT position | AA change | Cloned fragment[1] TP21 | | Cloned fragment[1] E5 | | RT-PCR fragments[2] TP21 | | RT-PCR fragments[2] E5 | Infectious clones[3] |
|---|---|---|---|---|---|---|---|---|---|---|
| 5'NCR | 35 | | G | | C | | C | | C | C |
| | 61 | | — | | G | | G | | G | G |
| C | 371 | Thr$_{80}$ > Pro | A | — | C | | A | | A | A |
| | 461 | Leu$_{110}$ > Ile | C | — | A | | C | | C | C |
| preM | 514 | | G | | U | | G | | G | G |
| | 957 | Val$_{160}$ > Ala | U | | U | | C | | C | C |
| E | 1325 | Phe$_{119}$ > Val | U | | U | | U | — | G | _U_* |
| | 1327 | | C | | A | | C | | A | C |
| | 1342 | | G | | A | | G | | A | G |
| | 1437 | Thr$_{156}$/Ile | C/U | | C | | C | | C | C |
| | 1567 | | A | | U | | U | | U | U |
| | 1823 | Gly$_{285}$ > Ser | G | — | A | | A | | A | A |
| | 1968 | Phe$_{333}$ > Ser | U | — | C | | C | | C | C |
| | 2135 | Asn$_{389}$ > Asp | A | — | G | ↔ | A | — | G | _A_ |
| NS1 | 3008 | Val$_{184}$ > Met | G | — | A | | A | | A | A |
| | 3403 | | C | | U | | C | | U | C |
| NS2A | 3635 | Pro$_{41}$ > Ala | C | — | G | | G | | G | G |
| | 3637 | | G | | C | | C | | C | C |
| | 3964 | | G | | A | | G | | G | G |
| NS3 | 4662 | Asn$_{22}$ > Ser | A | — | G | ↔ | A | — | G | _A_ |
| | 5340 | Phe$_{248}$ > Tyr | U | — | A | ↔ | U | — | A | _U_ |
| | 5374 | | C | | U | | C | | U | C |
| | 5546 | Phe$_{317}$ > Leu | U | — | C | ↔ | U | — | C | _U_ |
| NS5 | 8878 | | U | | U | | U | | G | U |
| | 8928 | Ser$_{422}$ > Thr | G | | G | | C | — | G | _G_ |
| | 9288 | Arg$_{542}$ > Lys | G | | G | | G | — | A | _G_ |
| 3'NCR | 10516-17 | | AC | | — | | AC | | AC | AC |
| | 10601 | | — | | C | | C | | C | C |
| | 10635 | | — | | U | | U | | U | U |
| | 10688-9 | | CG | | CG | | GC | | GC | GC |
| | 10761-2 | | AG | | AG | | CA | | CA | CA |
| | 10838-9 | | GU | | GU | | UC | | UC | UC |

[1]Sequence analysis of the cDNA fragments of LGT genome cloned in *E.coli* was described previously (Pletnev and Men, 1998). [2]Consensus sequence of viral genome was determined by sequencing RT-PCR-fragments derived from two separate preparations of virus which differed $10^{2-3}$ fold in titer (see Examples). Dominant base is shown at each indicated nucleotide position of genomic consensus sequence. Lesser amount of another base was occasionally detected at certain positions as indicated by double assignments, as for example at nt 1437. Nucleotide differences in consensus sequences between TP21 and E5 strains of LGT that resulted in a coding change difference are shown in bold letters. Numbering of nucleotides and amino acids is the same for strains TP21 and E5, because these viruses have the same number of nucleotides and amino acids. [3]Sequence of rescued 636, 649, 656 and 689 virus genomes was determined by analysis of cDNA fragments which were obtained by RT-PCR. *Sequence of 4 rescued cDNA LGT clones at position where TP21 and E5 differed in amino acid consensus sequence is underlined.

Note: — denotes a coding difference between TP21 and E5 at indicated position was determined for cloned genome segments and/or RT-PCR genome fragments. ↔ indicates the same coding difference was detected using these two methods of sequence analysis.

TABLE 2

Sequence variation that occurred during the rescue of infectious LGT TP21 from plasmid cDNA.

| Nucleotide position (genome) | Protein and amino acid position | Rescued virus differed from consensus sequence (determined by RT-PCR) at the indicated positions of the viral genome: (The same coding and non-coding differences were also present in plasmid cDNA used for virus rescue unless underlined.) 636 | 649 | 656 | 689 |
|---|---|---|---|---|---|
| $A_{590}$ | preM; $Met_{38}$ | | | G, Val | |
| $C_{1309}$ | E | | | U | |
| $A_{1893}$ | E; $Asp_{308}$ | | | C,Ala | |
| $C_{2083}$ | E | U | | | |
| $U_{2230}$ | E | | C | | C |
| $C_{2282}$ | E; $His_{438}$ | U,Tyr | | | |
| $A_{3001}$ | NS1 | | G | | G |
| $C_{3599}$ | NS2A; $Pro_{29}$ | | U,Ser | | U,Ser |
| $G_{3777}$ | NS2A; $Arg_{88}$ | | A,Lys | | |
| $C_{4192}$ | NS2A | | U | | |
| $G_{4254}$ | NS2B: $Ser_{17}$ | | A,Asn | | |
| $C_{4299}$ | NS2B; $Ala_{32}$ | U, Val | | | C/U, Val |
| $A_{4374}$ | NS2B; $Asn_{57}$ | | C,Thr | | |
| $C_{4429}$ | NS2B | | | U | |

TABLE 3

Neuroinvasiveness of parental LGT strains and cDNA-derived LGT TP21 virus clones in adult Swiss mice.

| Virus | Mortality* of mice after IP inoculation with $10^4$ or $10^6$ PFU of virus $10^4$ | $10^6$ |
|---|---|---|
| TP21 | 5/5 (100%) | 4**/5 (80%) |
| E5 | 0/5 | 0/5 |
| cDNA-derived TP21 clone: | | |
| 636 | 0/5 | 0/5 |
| 649 | 0/5 | 1/8 (12.5%) |
| 656 | 0/5 | 0/5 |
| 689 | nt | 2/5 (40%) |

*No. of mice that died/no. of mice tested (% mortality). **A mouse survived IP inoculation with TP21 but was paralyzed for 5 days and then recovered.

TABLE A

Mutations acquired when TP21/DEN4 and E5/DEN4 chimeras recovered in mosquito cells were adapted to grow efficiently in simian Vero cells.

| Region of viral genome | Nucleotide position | TP21/DEN4 virus grown in C6/36 cells | TP21/DEN4 virus grown in Vero cells[a] | E5/DEN4 virus grown in C6/36 cells | E5/DEN4 virus grown in Vero cell[a] | Amino acid change |
|---|---|---|---|---|---|---|
| C | 212[b] | | | U | C | |
| pre-M | 643 | | | G | A | |
| | 870 | | | U | C | $Phe_{151}$→Ser |
| E | 1437 | | | C | U | $Thr_{151}$→Ile[c] |
| | 1856 | A | C | A | C | $Lys_{296}$→Gln |

TABLE A-continued

Mutations acquired when TP21/DEN4 and E5/DEN4 chimeras recovered in mosquito cells were adapted to grow efficiently in simian Vero cells.

| Region of viral genome | Nucleotide position | TP21/DEN4 virus grown in C6/36 cells | TP21/DEN4 virus grown in Vero cells[a] | E5/DEN4 virus grown in C6/36 cells | E5/DEN4 virus grown in Vero cell[a] | Amino acid change |
|---|---|---|---|---|---|---|
| | 1898 | A | G | A | G | $Thr_{310}$→Ala |
| | 1973 | | | A | U | $Thr_{335}$→Ser |
| | 2371[b] | G | U | | | $Cys_{480}$→Phe |
| | 2403[b] | | | G | A | $Gly_{491}$→Ser |

[a]Virus recovered from cDNA in mosquito C6/36 cells and then passaged 5 times in simian Vero cells.
[b]Nucleotide number for DEN4 genome.
[c]Results in loss of potential glycosylation site.

TABLE B

Neourovinvasiveness of Vero cell grown LGT/DEN4 chimeras used for immunization.

| Mice | Virus | Vero cell-grown LGT strains and LGT/DEN4 chimeras tested: Amount of virus inoculated IP as determined in Vero cells (PFU) | % Mortality (No. dead/ No. tested) | Estimated $LD_{50}$ (PFU) | Previously determined neuro-invasiveness ($LD_{50}$) of mosquito cell grown LGT/DEN4 chimeras. IP $LD_{50}$ (PFU) determination based on titration in mosquito cells (ref.6)[a]. LGT strains TP21 and E5 were titered in Vero cells. |
|---|---|---|---|---|---|
| Swiss | TP21/ DEN4 (vac) | $5 \times 10^5$ | 0 (0/10) | $>5 \times 10^5$ | $>10^5$ |
| | E5/ DEN4 (vac) | $5 \times 10^5$ | 0 (0/5) | $>5 \times 10^5$ | $>10^5$ |
| | TP21 | $1 \times 10^5$ | 100 (10/10) | $<10^5$ | $5 \times 10^3$ |
| | E5 | $1 \times 10^5$ | 0 (0/5) | $>10^5$ | $>10^7$ |
| SCID | TP21/ DEN4 (vac) | $5 \times 10^5$ | 0 (0/10[b]) | $>5 \times 10^5$ | $>10^7$ |
| | E5/ DEN4 (vac) | $5 \times 10^5$ | 0 (0/10[b]) | $>5 \times 10^5$ | $>10^7$ |
| | TP21 | $1 \times 10^2$ | 100 (10/10) | $<10^2$ | $4 \times 10^{-3}$ |
| | E5 | $1 \times 10^2$ | 100 (10/10) | $<10^2$ | $6 \times 10^{-2}$ |

[a]Data from Pletnev and Men 1998 (Pletnev, A. G., and Men, R. (1998) Attenuation of the Langat tick-borne flavivirus by chimerization with mosquito-borne flavivirus dengue type 4. Proc. Natl. Acad. Sci. USA, 95, 1746–1751.) presented for purpose of comparison.
[b]Five surviving mice were challenged IP on day 50 with $10^2$ PFU of TP21 virus. All these mice died 10 to 13 days post challenge. Brain, liver and blood of the 5 remaining survivors were collected on day 50 and tested for viral genome by direct RT-PCR analysis and for viable virus by inoculation of Vero cell cultures that were analyzed by immunofluorescence for viral antigens 7 days later.

TABLE C

Intraperitoneal (IP) immunization of inbred mice with low dose of Langat TP21/DEN4(vac) chimera protects against subsequent IP challenge with highly virulent TBEV strain Absettarov.

| IP immunization | No. of inoculation (interval in days between inoculations) | Mouse strain | IP challenge with 320 PFU of TBEV on indicated day | | | |
|---|---|---|---|---|---|---|
| | | | Day of challenge | No. of mice | No. that survived (%) | Average survival time of mice that died (days) |
| 600 PFU of TP21/DEN4 (vac) chimera | 1 | BALB/c | 26 | 10 | 2 (20%) | 9.8 |
| | | CBA | 26 | 10 | 6 (60%) | 11.2 |
| | 2 (29) | BALB/c | 55 | 10 | 4 (40%) | 9.7 |
| | | CBA | 55 | 9 | 9 (100%) | |
| | 2 (26) | BALB/c | 94 | 10 | 6 (60%) | 12.5 |
| | 3 (29, 39) | BALB/c | 94 | 10 | 8 (80%) | 16 |
| | 4 (26, 66, 35) | BALB/c | 180 | 5 | 5 (100%) | |
| Tissue culture medium | | BALB/c | 26 | 10 | 0 (0%) | 8.1 |
| | | | 55 | 10 | 0 | |
| | | | 94 | 10 | 0 | |
| | | | 180 | 10 | 0 | |
| | | CBA | 26 | 9 | 0 | 10.2 |
| | | | 55 | 10 | 0 | |

TABLE D

Intraperitoneal (IP) immunization of Swiss mice with Langat (LGT)/DEN4 chimeras protects against subsequent IP challenge with highly virulent TBEV strain Sofjin.

| IP Immunization | | No. of inoculations (interval in days between inoculations) | Serum neutralizing antibody titer[a] (reciprocal geometric mean) | IP challenge with 100 $LD_{50}$ of TBEV on day 46 | | |
|---|---|---|---|---|---|---|
| Virus | Dose (PFU) | | | No. mice | No. that survived (%) | Average survival time of mice that died (days) |
| TP21 | $10^2$ | 1 | 1676 | 5 | 5 (100%) | |
| TP21/DEN4 (vac) | $10^5$ | 1 | 54 | 9 | 2 (22%) | 10.7 |
| | | 2 (22) | 452 | 6 | 6 (100%) | |
| E5 | $10^2$ | 1 | 489 | 10 | 10 (100%) | |
| E5/DEN4 (vac) | $10^5$ | 1 | 56 | 8 | 1 (12%) | 12.9 |
| | | 2 (22) | 96 | 6 | 4 (67%) | 11.0 |
| TP21-656[b] | $10^2$ | 1 | 831 | 10 | 9 (90%) | 10.0 |
| DEN4 | $10^5$ | 1 | <20 | 8 | 0 (0%) | 10.6 |
| Tissue culture medium | — | | <20 | 19 | 0 (0%) | 10.7 |

[a]Neutralizing antibodies in mouse serum collected 40 days after first immunization were measured by a 50% focus reduction neutralization test using TP21 virus.
[b]Mutant of cDNA-derived LGT strain TP21.

TABLE I

Changes from consensus sequence of E5 that occured during cloning, rescue of E5 from full-length cDNA and passage in simian Vero or chicken embryo fibroblast (CEF) cell culture.

| Genome region | NT position | Sequence of parental E5 | Deviation from E5 consesnsus sequence | | | | |
|---|---|---|---|---|---|---|---|
| | | | Plasmid pDNA | Rescued E5-651 isolated or passaged in | | | |
| | | | | Vero | | CEF | |
| | | | | Passage 1 | Passage 12 | Passage 1 | Passage 12 |
| 5'NCR | 53 | U | | | | | C |
| E | 1151 | C | | | | C/U | U |
| | 1358 | C | | | | | U($His_{130}$→Tyr) |
| | 1415 | G | | | | G/A($Glu_{149}$/Arg) | A($Glu_{149}$→Arg) |
| | 1416 | A | G($Glu_{149}$→Gly) | → | → | → | → |
| | 1485 | C | | | | | C/U($Thr_{172}$/Ile) |
| | 1842 | A | G($Glu_{291}$→Gly) | → | → | → | → |
| NS1 | 3046 | U | C | → | → | → | → |
| | 3154 | U | C | → | → | → | → |
| NS2B | 4254 | G | | | G/A($Ser_{17}$/Asn) | | |
| NS3 | 4528 | U | C | → | → | → | → |
| | 4675 | C | | | | | A |
| | 5744 | C | | | C/A($Gln_{383}$/Lys) | | |
| NS4B | 6955 | C | U | → | → | → | → |
| | 7294 | G | A | → | → | → | → |
| | 7455 | C | U($Ala_{183}$→Val) | → | → | → | → |

Note: Coding changes are positioned left of center whereas non-coding changes are positioned in the center of their respective columns. Long arrow denotes a coding or non-coding change that is conserved subsequently.

TABLE II

Lineage and reduction of neiroinvasiveness of Langat virus (LGT) during passage in eggs and subsequent recovery from full-length cDNA and deletion of 320 nt from its 3' non-coding region.

| LGT strain | Derivation | Plaque size[a] (mm) in simian cells: LLCMK$_2$ | Vero | Titer (FFU/ml)[b] attained in cell culture at 5 days: LLCMK$_2$ | Vero | Neuroinvasiveness of Vero cell grown virus for SCID mice inoculated IP: LD$_{50}$(PFU) | Fold reduction compared to: Immediate parent | TP21 |
|---|---|---|---|---|---|---|---|---|
| TP21 | Isolated from ticks | 5.0 | 4.0 | $2.8 \times 10^8$ | $1.9 \times 10^9$ | 0.004[c)] | | |
| E5 | 42 passages in eggs | 5.0 | 5.2 | $2.4 \times 10^7$ | $2.3 \times 10^8$ | 0.06[c)] | 15 | 15 |
| E5-651 | Recovered from full-length cDNA in Vero cells | 1.5 | <0.1 | $4.4 \times 10^6$ | $1.7 \times 10^8$ | 20.4 | 340 | 5,100 |
| E5-3'-320 | 320 nt deletion in 3' NCR of genome recovered in Vero cells | ~0.2 | No plaques | $5.0 \times 10^5$ | $1.5 \times 10^4$ | 479 | 23.5 | 119,750 |

[a)]Plaque size on day 7 post-infection.
[b)]Data were taken from growth curve analysis (shown in FIG. II) where MOI was 0.01 and virus titer in medium of infected cells was determined by a day 5 immunostaining focus-forming assay (see Examples).
[c)]Data from: Pletnev, A. G., and Men, R. (1998) Attenuation of the Langat tick-borne flavivirus by chimerization with mosquito-borne flavivirus dengue type 4. Proc. Natl. Acad. Sci. USA, 95,1746–1751.

TABLE III

Non-coding or coding changes in virus recovered from brain of moribund mice 14 or 28 days after IP inoculation of E5 or recombinant cDNA-derived E5-3'-320).

| | | Deviation of sequence of brain isolate from indicated virus inoculated 14[(a)] or 28[(b)] days previously | | | | |
|---|---|---|---|---|---|---|
| | | Uncloned E5 | Recombinant cDNA-derived clone E5-651 | | | Recombinant cDNA-derived clone E5-3'-320; |
| Genome region | Nucleotide position | Inoculum 16.7 LD$_{50}$[a)] | Inoculum 4.9 LD$_{50}$[b)] | Inoculum 49 LD$_{50}$[a)] | Inoculum 490 LD$_{50}$[a)] | Inoculum 2.1 LD$_{50}$[b)] |
| E | 1071 | | | C→C/U(Thr$_{34}$→Met) | | |
| | 1358 | | | | | C→U(His$_{130}$→Tyr) |
| | 1416 | | | | | G→A(Gly$_{149}$→Glu) |
| | 1571 | | G→(Ala$_{201}$→Thr) | G→G/A(Ala$_{201}$→Thr) | | |
| | 2175 | U→U/C(Val$_{402}$→Ala) | | | | |
| NS1 | 3381 | U→U/C(Val$_{308}$→Ala) | | | | |
| NS2A | 3523 | | G→A | G→G/A | | |
| | 3952 | | | | A→U | |
| NS2B | 4254 | | G→A(Ser$_{17}$→Asn) | | | |
| NS3 | 5518 | C→C/U | | | | |
| | 5794 | | G→U(Glu$_{399}$→Asp) | G→G/U(Glu$_{399}$→Asp) | | |
| | 5896 | | A→G | A→A/G | | |
| NS4B | 7432 | | C→C/U | | | |
| | 7455 | C→C/U(Ala$_{183}$→Val) | | | | |
| NS5 | 10333 | | C→U | | | |

Note: Coding changes are positioned left of center, whereas non-coding changes are positioned in the center of their respective columns.

TABLE IV

Antibody response and protective efficacy of LGT virus strains in Swiss mice.

| Immunizing virus | | Geometric mean of serum neutralizing | Mortality after IP challenge |
|---|---|---|---|
| Strain | Dose (PFU) | antibody titer (reciprocal)[a)] | with 2,000 IP $LD_{50}$ of TP21[b)] |
| E5 | $10^3$ | 448 | 0/5 |
| | $10^2$ | 237 | 0/5 |
| | 10 | 110 | 0/10 |
| E5-651 | $10^3$ | 372 | 0/10 |
| | $10^2$ | 152 | 0/10 |
| | 10 | 130 | 0/10 |

TABLE IV-continued

Antibody response and protective efficacy of LGT virus strains in Swiss mice.

| Immunizing virus | | Geometric mean of serum neutralizing | Mortality after IP challenge |
|---|---|---|---|
| Strain | Dose (PFU) | antibody titer (reciprocal)[a)] | with 2,000 IP $LD_{50}$ of TP21[b)] |
| E5-3'-320 | $10^4$ | 363 | 0/9 |
| | $10^3$ | 282 | 0/10 |
| | $10^2$ | 271 | 0/9 |
| | 10 | 225 | 0/10 |
| Control | NA | <20 | 9/9 |

[a)]Neutralizing antibodies in mouse serum collected 22 days after immunization were measured by a 50% focus reduction test using TP21 virus.
[b)]Number of mice that died/numer of mice tested.

What is claimed is:

1. A full-length infectious cDNA clone of Langat tick-borne flavivirus.

2. The clone of claim 1, wherein said Langat is Langat strain TP21.

3. The clone of claim 1, wherein said Langat is Langat strain E5.

4. The clone of claim 1, further comprising at least one virulence-reducing mutation that is less virulent than TP21, whether spontaneously arising or genetically engineered.

5. The clone of claim 1, incorporated within a vector.

6. The clone of claim 5, wherein said vector is a plasmid.

7. A prokaryotic host cell transformed with the clone of claim 1.

8. A full-length infectious RNA transcribed from a full-length cDNA clone of Langat tick-borne flavivirus.

9. A eucaryotic host cell infected with the RNA of claim 8.

10. A virus produced from the host cell of claim 9.

11. A unit dose of an immunogenic composition comprising the virus of claim 10.

12. A method of inducing an immune response comprising the step of administering the unit dose of claim 11 to a vaccinee.

13. A method of making a full-length infectious cDNA clone of Langat tick-borne flavivirus comprising as a first step the step of harvesting a Langat tick-borne flavivirus suspension early in the growth cycle to minimize the frequency of deletion mutants that accumulate late in infection.

14. The method of claim 13, wherein the viral titer of the flavivirus suspension is about $3.8\times10^3$ PFU.

15. The clone of claim 1 comprising the mutations of TP21-636.

16. The clone of claim 1 comprising the mutations of TP21-649.

17. The clone of claim 1 comprising the mutations of TP21-656.

18. The clone of claim 1 comprising the mutations of TP21-689.

19. The clone of claim 1 comprising the mutations of E5-651.

20. The clone of claim 1 comprising the mutations of E5-3'-320.

* * * * *